United States Patent
Hu (12)

(10) Patent No.: US 7,368,462 B1
(45) Date of Patent: May 6, 2008

(54) MELANIN CONCENTRATING HORMONE ANTAGONISTS

(75) Inventor: Xiufeng Eric Hu, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 50 days.

(21) Appl. No.: 11/180,814

(22) Filed: Jul. 13, 2005

Related U.S. Application Data

(60) Provisional application No. 60/588,209, filed on Jul. 15, 2004.

(51) Int. Cl.
| | |
|---|---|
| *A61K 31/451* | (2006.01) |
| *A61K 31/402* | (2006.01) |
| *A61K 31/166* | (2006.01) |
| *C07D 207/06* | (2006.01) |
| *C07D 211/10* | (2006.01) |
| *C07C 211/57* | (2006.01) |

(52) U.S. Cl. ............... 514/319; 514/429; 514/617; 546/195; 548/567; 564/337

(58) Field of Classification Search ............... 546/184, 546/195; 548/567; 564/337; 514/357, 429, 514/319
See application file for complete search history.

(56) References Cited

OTHER PUBLICATIONS

CAPLUS listing AN:2003:319711, "Preparation of 2'-methyl-5'-(1,3,4-oxadiazol-2-yl)-1, 1'-biphenyl-4-carboxamides as p38 kinase inhibitors," Angell et al. (2003).*

* cited by examiner

*Primary Examiner*—Kamal A. Saeed
*Assistant Examiner*—Janet L. Coppins
(74) *Attorney, Agent, or Firm*—Cynthia L. Clay; Kelly L. McDow

(57) ABSTRACT

The present invention relates to compounds capable of serving as moderators of human and mammalian appetite and as such provide a means for reducing body mass and controlling obesity.

14 Claims, No Drawings

MELANIN CONCENTRATING HORMONE ANTAGONISTS

CROSS REFERENCE TO RELATED APPLICATIONS

This application claims priority under Title 35, United States Code 119(e) from Provisional Application Ser. No. 60/588,209, filed Jul. 15, 2004.

FIELD OF THE INVENTION

The present invention relates to compounds capable of serving as moderators of human and mammalian appetite and as such provides a means for reducing body mass. The compounds of the present invention are selective against melanin concentrating hormone (MCH) while not having the pernicious side effects which results from undesirable interactions at other appetite-related brain receptors.

DETAILED DESCRIPTION OF THE INVENTION

The present invention relates to the surprising discovery that certain compounds (compositions of matter, analogs) bind selectively as antagonists to the MCH-R1 receptor without substantial binding to the 5-HT$_{2c}$ receptor. What is meant herein by "selective binding" is binding to the MCH-R1 receptor at a level at least about 10 fold greater than at the 5-HT$_{2c}$ receptor. For example, a compound with an IC-50 at MCH-R1 of 12 nM and an IC-50 at 5-HT$_{2c}$ of 1125 nM would be a compound which is within the range of compounds considered to be a selective antagonist at the MCH-R1 receptor over the 5-HT$_{2c}$ receptor.

The present invention encompasses three major aspects each of which have their own separate categories, aspects, iterations, and specific iterative examples. The major aspects of the present invention include:
  i) compositions of matter which are selective antagonists for MCH-R1 receptors over 5-HT$_{2c}$ receptors;
  ii) compositions and pharmaceutical compositions (matrices) comprising said compositions of matter, and
  iii) methods for controlling, abating, preventing, or otherwise alleviating diseases or the symptoms of disease states related to body mass, said diseases or the symptoms of disease states being controlled by administration of said compositions of matter to a human or mammal, whether said composition of matter is administered alone or in a composition or within a pharmaceutical composition (matrix).

The following chemical hierarchy is used throughout the specification to particularly point out and distinctly claim the units which comprise the compounds of the present invention. The term "hydrocarbyl" stands for any carbon atom-based unit (organic molecule), said units optionally containing one or more organic functional groups, including inorganic atom comprising salts, inter alia, carboxylate salts, quaternary ammonium salts. Encompassed within the term "hydrocarbyl" are the terms "acyclic" and "cyclic" units which divide hydrocarbyl units into cyclic and non-cyclic classes.

1. Substituted and unsubstituted $C_1$-$C_{10}$ acyclic hydrocarbyl:
   For the purposes of the present invention the term "substituted and unsubstituted $C_1$-$C_{10}$ acyclic hydrocarbyl" encompasses 3 categories of units:
   i) $C_1$-$C_{10}$ linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted $C_1$-$C_{10}$ linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
   ii) $C_2$-$C_{10}$ linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted $C_2$-$C_{10}$ linear or branched alkenyl, non-limiting examples of which includes, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
   iii) $C_2$-$C_{10}$ linear or branched alkynyl, non-limiting examples of which include, ethynyl ($C_2$), prop-2-ynyl (also propargyl) ($C_3$), propyn-1-yl ($C_3$), and 2-methylhex-4-yn-1-yl ($C_7$); substituted $C_2$-$C_{10}$ linear or branched alkynyl, non-limiting examples of which includes, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

2. Substituted and unsubstituted $C_1$-$C_{10}$ cyclic hydrocarbyl:
   For the purposes of the present invention the term "substituted and unsubstituted $C_1$-$C_{10}$ cyclic hydrocarbyl" encompasses 5 categories of units:
   i) $C_3$-$C_{10}$ carbocyclic units, non-limiting examples of which include, cyclopropyl ($C_3$), cyclobutyl ($C_4$), cyclopentyl ($C_5$), cyclohexyl ($C_6$), cycloheptyl ($C_7$), decalinyl ($C_{10}$), decahydro-azulenyl ($C_{10}$), and the like; substituted $C_3$-$C_{10}$ carbocyclic units, non-limiting examples of which includes, 2-methylcyclopropyl ($C_3$), 2,5-dimethylcyclopentyl ($C_5$), 4-tert-butylcyclopentyl ($C_5$), 3,5-dichlorocyclohexyl ($C_6$), 4-hydroxy-cyclohexyl ($C_6$), and the like.
   ii) $C_6$-$C_{10}$ aryl units which include, phenyl, naphthen-1-yl, and naphthen-2-yl; substituted $C_6$-$C_{10}$ aryl units, non-limiting examples of which includes, 4-fluorophenyl ($C_6$), 2,6-di-tert-butylphenyl ($C_6$), 3-hydroxyphenyl ($C_6$), 8-hydroxynaphthylen-2-yl ($C_{10}$), 6-cyano-naphthylen-1-yl ($C_{10}$), and the like.
   iii) $C_1$-$C_{10}$ heterocyclic units, non-limiting examples of which include, 1,2,3,4-tetrazolyl ($C_1$), aziridinyl ($C_2$), oxazolyl ($C_3$), tetrahydrofuranyl ($C_4$), dihydropyranyl ($C_5$), piperidin-2-one (valerolactam) ($C_5$), 2,3,4,5-tetrahydro-1H-azepinyl ($C_6$), 2,3-dihydro-1H-indole ($C_8$), 1,2,3,4-tetrahydro-quinoline ($C_9$), and the like; substituted $C_1$-$C_{10}$ heterocyclic units, non-limiting examples of which include, 2-amino-4,5-dihydro-3H-pyrrolyl ($C_4$), N-methylmorpholinyl ($C_4$), 2,6-dimethylpiperazinyl ($C_4$), and the like.
   iv) $C_1$-$C_{10}$ heteroaryl units, non-limiting examples of which include: triazinyl ($C_3$), furanyl ($C_4$), thiophenyl ($C_4$), pyrimidinyl ($C_4$), pyridinyl ($C_5$), 6,7-dihydro-5H-cyclopenta[b]pyridine ($C_8$), and the like; substituted $C_1$-$C_{10}$ heteroaryl units, non-limiting examples of which include, 4-dimethylaminopyridinyl ($C_5$), 2-methylindolyl ($C_8$), and the like.
   v) $C_1$-$C_{12}$ tethered cyclic hydrocarbyl units (whether $C_3$-$C_{10}$ carbocyclic units, $C_6$-$C_{10}$ aryl units, $C_1$-$C_{10}$ heterocyclic units, or $C_1$-$C_{10}$ heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

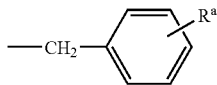

wherein $R^a$ is optionally one or more independently chosen substitutions for hydrogen. Further examples include other aryl units, inter alia, naphthalen-2-ylmethyl $C_1$-($C_{10}$), 4-fluorobenzyl $C_1$-($C_6$), 2-(3-hydroxyphenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl, for example a 2-picolyl $C_1$-($C_6$) unit having the formula:

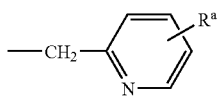

wherein $R^a$ is the same as defined above. In addition, $C_1$-$C_{12}$ tethered cyclic hydrocarbyl units include $C_1$-$C_{10}$ alkyleneheterocyclic units, non-limiting examples of which include, aziridinylmethyl $C_1$-($C_2$) and oxazol-2-ylmethyl $C_1$-($C_3$).

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

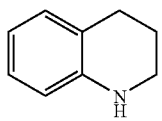

is, for the purposes of the present invention, considered a heterocyclic unit. 6,7-Dihydro-5H-cyclopenta[b]pyridine having the formula:

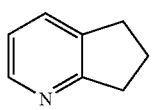

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

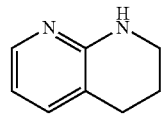

is, for the purposes of the present invention, considered a heteroaryl unit.

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. A unit which encompasses a three hydrogen atom replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of units which can substitute for hydrogen atoms on a hydrocarbyl or other unit:

i) —$OR^{11}$;
ii) —$C(O)R^{11}$;
iii) —$C(O)OR^{11}$
iv) —$C(O)N(R^{11})_2$;
v) —CN;
vi) —$N(R^{11})_2$;
vii) -halogen;
viii) —$CF_3$, —$CCl_3$, —$CBr_3$; and
ix) —$SO_2R^{11}$ wherein each $R^{11}$ is independently hydrogen, substituted or unsubstituted $C_1$-$C_4$ linear, branched, or cyclic alkyl; or two $R^{11}$ units can be taken together to form a ring comprising 3-7 atoms.

As described further herein below, $R^5$ units represent substitutes for hydrogen atoms on the $R^3$ moieties. When the index n is greater than 0, from 1 to 5 hydrogen atoms on the rings are capable of being substituted by any substituent.

Melanin Concentrating Hormone Antagonists

The compounds of the present invention are melanin concentrating hormone antagonists and comprise all enantiomeric and diasteriomeric forms and salts thereof, said antagonists having the principal naphthalene scaffold with the formula:

wherein said melanin concentrating hormone antagonists have three principal parts:

a) R units having the formula:

wherein $R^3$ comprises an aryl unit chosen from:
  i) substituted or unsubstituted phenyl units having the formula:

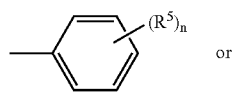

ii) substituted or unsubstituted biphenyl units having the formula:

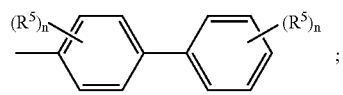

the index x is 0 or 1, each index n is independently from 0 to 5;

b) a core N-(6-substituted-naphthalen-1-yl)methylene amide unit having the formula:

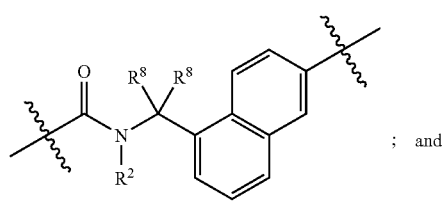

c) an amino unit comprising a basic nitrogen atom having the formula:

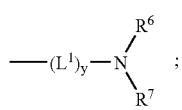

the index y is 0 or 1.

Substituted or Unsubstituted Aryl Units

A first principal element of the MCH antagonists of the present invention relates to R units having the formula:

wherein $R^3$ is a substituted or unsubstituted aryl unit chosen from:
  i) phenyl units having the formula:

ii) biphenyl units having the formula:

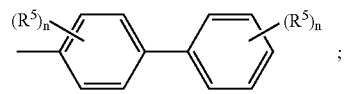

and L is an optionally present linking group defined herein below. When the index x is equal to 1 the linking unit L is present and serves to link $R^3$ to the core N-(6-substituted-naphthalen-1-yl)methylene amide unit.

First Category of R Units

The first category of R units relates to substituted and unsubstituted biphenyl units which are absent the L linking unit (index x=0), said unit having the formula:

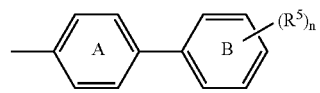

wherein the B-ring of the biphenyl unit either comprises all hydrogen atoms (index n=0) or the B-ring is substituted with from 1 to 5 units for hydrogen. The substitutes as defined herein above are each considered suitable substitutes for hydrogen atoms on the B-ring.

Aspect 1 of this category of R units relates to units having no substitutions for hydrogen (index n=0) wherein R is a 4-biphenyl unit.

Aspect 2 of this category of R units relates to units having one or more substitutes $R^5$ present wherein $R^5$ is a unit chosen from:
  i) halogen; for example, fluoro, chloro, or bromo;
  ii) $C_1$-$C_3$ linear or branched alkyl; for example, methyl ($C_1$), ethyl ($C_2$), n-propyl ($C_3$), or isopropyl ($C_3$);
  iii) $C_1$-$C_3$ linear or branched alkoxy; for example, methoxy ($C_1$), ethoxy ($C_2$), n-propoxy ($C_3$), or isopropoxy ($C_3$);
  iv) $C_1$-$C_2$ haloalkyl; for example, trifluoromethyl ($C_1$), 2,2,2-trifluorethyl ($C_2$), and trichloromethyl ($C_1$);
  v) cyano;
  vi) hydroxyl; and
  vii) —$CO_2R^9$ wherein $R^9$ is hydrogen or $C_1$-$C_4$ linear, branched, or cyclic alkyl, said units chosen from methyl, ethyl, n-propyl, isopropyl, n-butyl, isobutyl, and tert-butyl.

A first iteration of Aspect 2 relates to 4'-($R^5$-substituted)-biphenyl units, for example, 4'-fluoro-biphenyl having the formula:

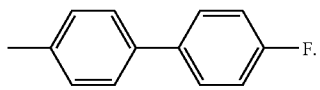

Further non-limiting examples according to this iteration include 4'-chloro-4-biphenyl, 4'-trifluoromethyl-4-biphenyl, 4'-cyano-4-biphenyl, 4'-nitro-4-biphenyl, 4'-methyl-4-biphenyl, and 4'-methoxy-4-biphenyl.

A second iteration of Aspect 2 relates to 3'-($R^5$-substituted)-biphenyl units, for example, 3'-fluoro-biphenyl having the formula:

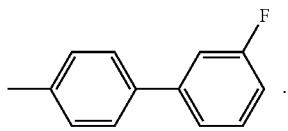

Further non-limiting examples according to this iteration include 3'-chloro-4-biphenyl, 3'-trifluoromethyl-4-biphenyl, 3'-cyano-4-biphenyl, 3'-nitro-4-biphenyl, and 3'-methoxy-4-biphenyl.

A third iteration of Aspect 2 relates to 2'-($R^5$-substituted)-biphenyl units, for example, 2'-fluoro-biphenyl having the formula:

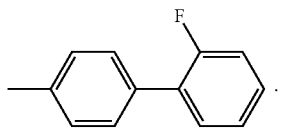

Further non-limiting examples according to this iteration include 2'-chloro-4-biphenyl, 2'-trifluoromethyl-4-biphenyl, 2'-cyano-4-biphenyl, 2'-nitro-4-biphenyl, and 2'-methoxy-4-biphenyl.

A fourth iteration of Aspect 2 relates to 3',4'-di-($R^5$-substituted)-biphenyl units, for example, 3',4'-difluoro-biphenyl having the formula:

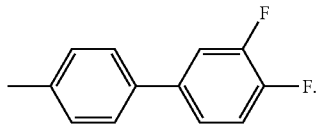

Further non-limiting examples according to this iteration include 3',4'-dichloro-4-biphenyl, 3'-nitro-4'-chloro-4-biphenyl, 3'-methoxy-4'-fluoro-4-biphenyl, 3',4'-ditrifluoromethyl-4-biphenyl, 3',4'-dicyano-4-biphenyl, 3',4'-dinitro-4-biphenyl, and 3',4'-dimethoxy-4-biphenyl.

Other Aspects which relate to the first category of R units are, however, not limited to those described herein above. For example, 3',5'-difluoro-biphenyl-4-carboxylic acid (6-dimethylaminomethyl-naphthalen-1-ylmethyl)-amide, a compound encompassed within the present invention, would be included in a further aspect, and can be formed by the procedure of Scheme I wherein 3',5'-difluoro-biphenyl-4-carboxylic acid is substituted for 4'-fluoro-biphenyl-4-carboxylic acid.

Second Category of R Units

The second category of R units relates to units having the formula:

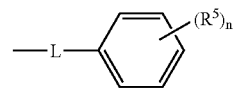

wherein a linking unit as defined herein below is present (index x=1) and one or more $R^5$ units are present, said $R^5$ units chosen from:

i) halogen; for example, fluoro, chloro, or bromo;

ii) $C_1$-$C_3$ linear or branched alkyl; for example, methyl ($C_1$), ethyl ($C_2$), n-propyl ($C_3$), or isopropyl ($C_3$);

iii) $C_1$-$C_3$ linear or branched alkoxy; for example, methoxy ($C_1$), ethoxy ($C_2$), n-propoxy ($C_3$), or isopropoxy ($C_3$);

iv) $C_1$-$C_2$ haloalkyl; for example, trifluoromethyl ($C_1$), 2,2,2-trifluorethyl ($C_2$), and trichloromethyl ($C_1$);

v) cyano; and vi) hydroxyl.

Aspect 1 of this category of R units relates to 4-($R^5$-substituted)phenyl units, for example, 4-fluorophenyl having the formula:

Further non-limiting examples according to Aspect 1 include 4-chlorophenyl, 4-methyl-phenyl, 4-methoxyphenyl, 4-trifluoromethylphenyl, 4-cyanophenyl, and 4-hydroxyphenyl.

Aspect 2 of this category of R units relates to di-substituted phenyl units, for example, 3,4-difluorophenyl having the formula:

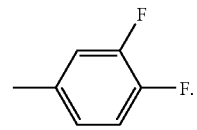

Further non-limiting examples of Aspect 2 include 2,4-difluorophenyl, 2,6-difluorophenyl, 3,5-difluorophenyl, 2-methoxy-3-chlorophenyl, and 2-cyano-3-methoxyphenyl.

Core N-(6-substituted-naphthalen-1-yl)methylene Amide Units

A second principal element of the MCH antagonists of the present invention relates to the N-(6-substituted-naphthalen-1-yl)methylene amide units having the formula:

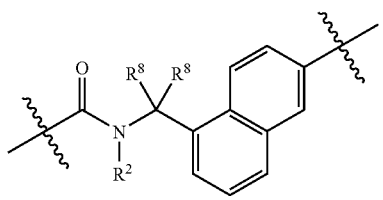

wherein $R^2$ is a unit chosen from:

i) hydrogen; or ii) $C_1$-$C_4$ linear, branched, or cyclic alkyl;

each $R^8$ is independently chosen from:

i) hydrogen;

ii) $C_1$-$C_6$ substituted or unsubstituted linear, branched, or cyclic hydrocarbyl;

iii) —$CO_2R^9$;

iv) two $R^8$ units can be taken together to form a carbonyl group;

$R^9$ is hydrogen or $C_1$-$C_4$ linear, branched, or cyclic alkyl; for example, methyl, ethyl, n-propyl, isopropyl, n-butyl, isobutyl, tert-butyl, cyclopropyl, cyclopropylmethyl, and cyclobutyl.

The N-(6-substituted-naphthalen-1-yl)methylene amide units are the core and together with the 4'-substituted-4-biphenyl units and amino units comprising a basic nitrogen atom, make up the compounds of the present invention.

First Category of Core Units

The first category of the core units relates to core units having the formula:

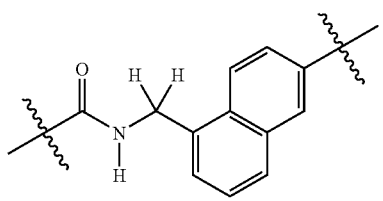

wherein $R^2$ is hydrogen and each $R^8$ unit is hydrogen. Compounds comprising Category I of the invention as described herein below contain a N-(6-substituted-naphthalen-1-yl)methylene unit as their core unit.

Second Category of Core Units

The second category of the core units relates to core units having the formula:

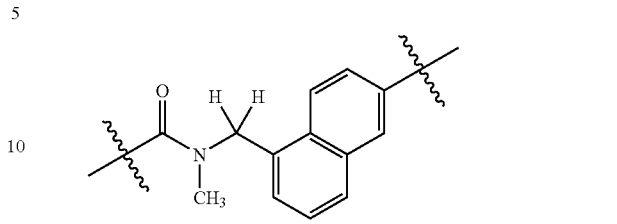

wherein $R^2$ is methyl and each $R^8$ unit is hydrogen. Compounds comprising Category II of the invention as described herein below contain a N-(6-substituted-naphthalen-1-yl) methylene unit as their core unit.

Amino Units Comprising a Basic Nitrogen Atom

A third principal element of the MCH antagonists of the present invention relates to the $R^1$ amino units comprising a basic nitrogen atom having the formula:

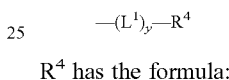

$R^4$ has the formula:

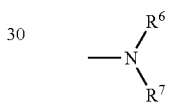

$R^6$ and $R^7$ are each independently chosen from:
i) hydrogen;
ii) $C_1$-$C_8$ substituted or unsubstituted linear, branched, or cyclic hydrocarbyl; for example, methyl, ethyl, n-propyl, isopropyl, n-butyl, isobutyl, tert-butyl, cyclopropyl, cyclopropylmethyl, cyclobutyl, and the like;
iii) substituted or unsubstituted $C_6$ or $C_{10}$ aryl; or $R^6$ and $R^7$ can be taken together to form a substituted or unsubstituted heterocyclic ring having from 3 to 8 atoms; the index y is 0 or 1.

Aspect 1 of $R^1$ units relates to units wherein $R^6$ and $R^7$ are each independently hydrogen or $C_1$-$C_8$ linear hydrocarbyl.

The first iteration of Aspect 1 relates to $R^6$ and $R^7$ are each independently chosen from hydrogen, methyl, and ethyl. This iteration includes amino units chosen from —$NH_2$, —$NH(CH_3)$, —$NH(CH_2CH_3)$, —$N(CH_3)_2$, —$N(CH_3)(CH_2CH_3)$, and —$N(CH_2CH_3)_2$.

The second iteration of Aspect 1 relates to $R^6$ and $R^7$ are each independently chosen from hydrogen, propyl, isopropyl, n-butyl, and n-pentyl. This iteration includes amino units chosen from —$NH(CH_2CH_2CH_3)$, —$N(CH_2CH_2CH_3)_2$, —$NH[CH_2(CH_3)_2]$, —$N[CH_2(CH_3)_2]_2$, —$NH(CH_2CH_2CH_2CH_3)$, —$N(CH_2CH_2CH_2CH_3)_2$, and —$N[(CH_2)_4CH_3]_2$.

Aspect 2 of $R^1$ units relates to units wherein $R^6$ and $R^7$ are taken together to form a heterocyclic ring having from 3 to 8 atoms. Non-limiting examples of rings which can be formed from $R^6$ and $R^7$ include: aziridin-1-yl, azetidin-1-yl, pyrrolidin-1-yl, 3-pyrrolin-1-yl, imidazolidin-1-yl, pyrazolidin-1-yl, piperidine-1-yl, piperazin-1-yl, 4-substituted-piperazin-1-yl, azepan-1-yl, and morpholin-4-yl.

Linking Units

L and $L^1$ are linking units each of which is selected independently of the other. When the index x is equal to 0, L is absent; when x is equal to 1, L is present. When the index y is equal to 0, $L^1$ is absent; when y is equal to 1, $L^1$ is present.

L and $L^1$ when present have the formula:

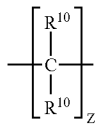

wherein each $R^{10}$ is independently chosen from:

i) hydrogen;

ii) $C_1$-$C_6$ substituted or unsubstituted linear, branched, or cyclic hydrocarbyl;

iii) —$CO_2R^9$;

iv) —CN;

two $R^{10}$ units on the same carbon are be taken together to form a carbonyl group; or $R^{10}$ units from two adjacent linking units are taken together to form a double bond;

$R^9$ is hydrogen or $C_1$-$C_4$ linear, branched, or cyclic alkyl.

The index z indicates the number of L or $L^1$ units which are present. The index z has the value form 1 to 3. For example, when an L or $L^1$ unit is present and the index z for that unit is equal to 1, the L or $L^1$ unit will have the formula:

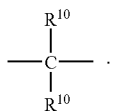

Likewise when the index z is equal to 2, the L or $L^1$ unit which is present will have the formula:

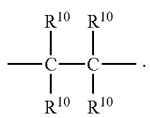

Aspect 1 of linking units relates to compounds comprising $L^1$ units (y=1) wherein $L^1$ is a methylene unit which is formed when the index z=1 and each $R^{10}$ unit is hydrogen. Taken together with the attached $R^4$ unit, this combination provides $R^1$ units having the formula:

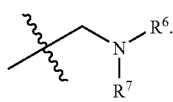

Aspect 1 of linking units relates to both Category I and Category II compounds of the present invention having the formula:

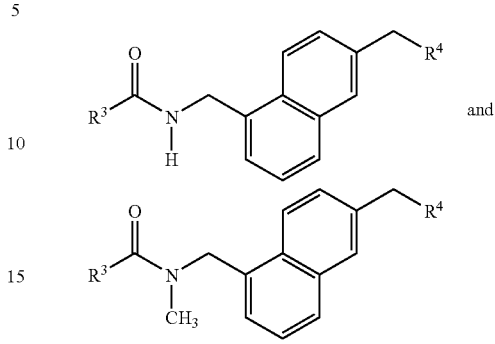

wherein L is absent (x=0) and $L^1$ is a methylene unit.

Aspect 2 of linking units relates to compounds wherein L is a unit having the formula:

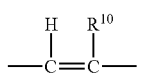

and $R^{10}$ is a unit selected from hydrogen, —CN, —$CH_3$, or —$NO_2$. A non-limiting example of an analog according to the present invention comprising the second aspect of linking units is 2-cyano-N-methyl-3-phenyl-N-(6-pyrrolidin-1-ylmethyl-naphthalen-1-ylmethyl)-acrylamide. The compounds of Aspect 2 also contain an $L^1$ unit which is a methylene unit.

As it relates to nomenclature, the compounds of the present invention are 6-(amino unit comprising)-1-amidomethyl-naphthalenes having the general formula:

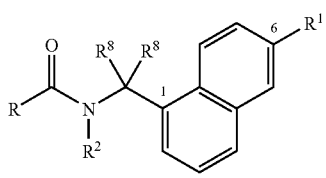

wherein R comprises an aryl unit, $R^1$ comprises a basic amino nitrogen, and $R^2$ is hydrogen or a hydrocarbyl unit described herein below. The compounds of the present invention, as named herein, are given chemical names which are viewed as derivatives of the R unit carboxylic acid, for example, the compound having the formula:

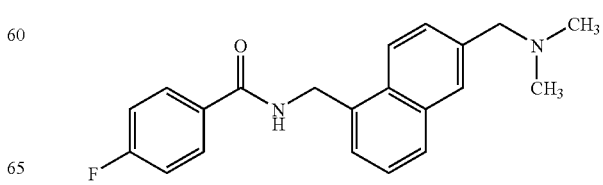

is named herein as N-(6-dimethylaminomethyl-naphthylen-1-ylmethyl)-4-fluorobenzamide and the compound having the formula:

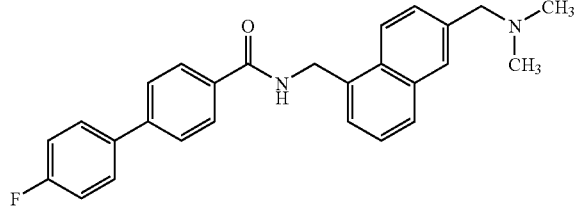

is named 4'-Fluoro-biphenyl-4-carboxylic acid (6-dimethylaminomethyl-naphthalen-1-ylmethyl)-amide. However, any exceptions to this naming scheme will be clear to the artisan of ordinary skill and not diminish from the description of the present invention.

Analog Categories

The analogs (compounds) of the present invention are arranged in several categories to assist the formulator in applying a rational synthetic strategy for the preparation of analogs which are not expressly exemplified herein. The arrangement into categories does not imply increased or decreased efficacy or utility for any of the compositions of matter, compositions, or methods described herein.

Category I of the present invention relates to compounds with a core scaffold having the formula:

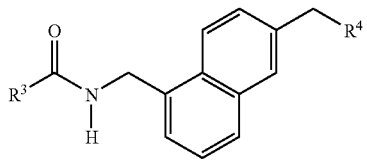

wherein L is absent and the $R^3$ unit is a substituted biphenyl thereby providing a core scaffold with the general formula:

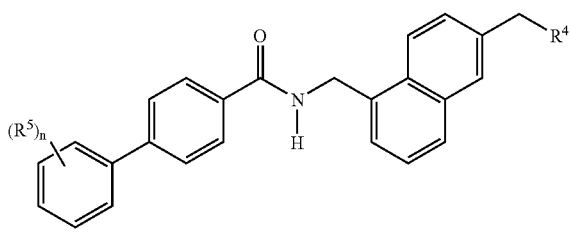

The first aspect of Category I relates to $R^4$ units having the formula:

wherein $R^6$ and $R^7$ units each independently comprise hydrogen or $C_1$-$C_8$ substituted or unsubstituted linear or branched hydrocarbyl as further described herein below in Table I.

TABLE I

| No. | $R^3$ | $R^4$ |
|---|---|---|
| 1 | 4-biphenyl | —NH$_2$ |
| 2 | 4-biphenyl | —NHCH$_3$ |
| 3 | 4-biphenyl | —N(CH$_3$)$_2$ |
| 4 | 4-biphenyl | —NH(C$_2$H$_5$) |
| 5 | 4-biphenyl | —N(C$_2$H$_5$)$_2$ |
| 6 | 3'-fluoro-4-biphenyl | —NH$_2$ |
| 7 | 3'-fluoro-4-biphenyl | —NHCH$_3$ |
| 8 | 3'-fluoro-4-biphenyl | —N(CH$_3$)$_2$ |
| 9 | 3'-fluoro-4-biphenyl | —NH(C$_2$H$_5$) |
| 10 | 3'-fluoro-4-biphenyl | —N(C$_2$H$_5$)$_2$ |
| 11 | 3'-chloro-4-biphenyl | —NH$_2$ |
| 12 | 3'-chloro-4-biphenyl | —NHCH$_3$ |
| 13 | 3'-chloro-4-biphenyl | —N(CH$_3$)$_2$ |
| 14 | 3'-chloro-4-biphenyl | —NH(C$_2$H$_5$) |
| 15 | 3'-chloro-4-biphenyl | —N(C$_2$H$_5$)$_2$ |
| 16 | 3'-trifluoromethyl-4-biphenyl | —NH$_2$ |
| 17 | 3'-trifluoromethyl-4-biphenyl | —NHCH$_3$ |
| 18 | 3'-trifluoromethyl-4-biphenyl | —N(CH$_3$)$_2$ |
| 19 | 3'-trifluoromethyl-4-biphenyl | —NH(C$_2$H$_5$) |
| 20 | 3'-trifluoromethyl-4-biphenyl | —N(C$_2$H$_5$)$_2$ |
| 21 | 3'-cyano-4-biphenyl | —NH$_2$ |
| 22 | 3'-cyano-4-biphenyl | —NHCH$_3$ |
| 23 | 3'-cyano-4-biphenyl | —N(CH$_3$)$_2$ |
| 24 | 3'-cyano-4-biphenyl | —NH(C$_2$H$_5$) |
| 25 | 3'-cyano-4-biphenyl | —N(C$_2$H$_5$)$_2$ |
| 26 | 3'-nitro-4-biphenyl | —NH$_2$ |
| 27 | 3'-nitro-4-biphenyl | —NHCH$_3$ |
| 28 | 3'-nitro-4-biphenyl | —N(CH$_3$)$_2$ |
| 29 | 3'-nitro-4-biphenyl | —NH(C$_2$H$_5$) |
| 30 | 3'-nitro-4-biphenyl | —N(C$_2$H$_5$)$_2$ |
| 31 | 3'-methoxy-4-biphenyl | —NH$_2$ |
| 32 | 3'-methoxy-4-biphenyl | —NHCH$_3$ |
| 33 | 3'-methoxy-4-biphenyl | —N(CH$_3$)$_2$ |
| 34 | 3'-methoxy-4-biphenyl | —NH(C$_2$H$_5$) |
| 35 | 3'-methoxy-4-biphenyl | —N(C$_2$H$_5$)$_2$ |
| 36 | 4'-fluoro-4-biphenyl | —NH$_2$ |
| 37 | 4'-fluoro-4-biphenyl | —NHCH$_3$ |
| 38 | 4'-fluoro-4-biphenyl | —N(CH$_3$)$_2$ |
| 39 | 4'-fluoro-4-biphenyl | —NH(C$_2$H$_5$) |
| 40 | 4'-fluoro-4-biphenyl | —N(C$_2$H$_5$)$_2$ |
| 41 | 4'-chloro-4-biphenyl | —NH$_2$ |
| 42 | 4'-chloro-4-biphenyl | —NHCH$_3$ |
| 43 | 4'-chloro-4-biphenyl | —N(CH$_3$)$_2$ |
| 44 | 4'-chloro-4-biphenyl | —NH(C$_2$H$_5$) |
| 45 | 4'-chloro-4-biphenyl | —N(C$_2$H$_5$)$_2$ |
| 46 | 4'-trifluoromethyl-4-biphenyl | —NH$_2$ |
| 47 | 4'-trifluoromethyl-4-biphenyl | —NHCH$_3$ |
| 48 | 4'-trifluoromethyl-4-biphenyl | —N(CH$_3$)$_2$ |
| 49 | 4'-trifluoromethyl-4-biphenyl | —NH(C$_2$H$_5$) |
| 50 | 4'-trifluoromethyl-4-biphenyl | —N(C$_2$H$_5$)$_2$ |
| 51 | 4'-cyano-4-biphenyl | —NH$_2$ |
| 52 | 4'-cyano-4-biphenyl | —NHCH$_3$ |
| 53 | 4'-cyano-4-biphenyl | —N(CH$_3$)$_2$ |
| 54 | 4'-cyano-4-biphenyl | —NH(C$_2$H$_5$) |
| 55 | 4'-cyano-4-biphenyl | —N(C$_2$H$_5$)$_2$ |
| 56 | 4'-nitro-4-biphenyl | —NH$_2$ |
| 57 | 4'-nitro-4-biphenyl | —NHCH$_3$ |
| 58 | 4'-nitro-4-biphenyl | —N(CH$_3$)$_2$ |
| 59 | 4'-nitro-4-biphenyl | —NH(C$_2$H$_5$) |
| 60 | 4'-nitro-4-biphenyl | —N(C$_2$H$_5$)$_2$ |
| 61 | 4'-methoxy-4-biphenyl | —NH$_2$ |
| 62 | 4'-methoxy-4-biphenyl | —NHCH$_3$ |
| 63 | 4'-methoxy-4-biphenyl | —N(CH$_3$)$_2$ |
| 64 | 4'-methoxy-4-biphenyl | —NH(C$_2$H$_5$) |
| 65 | 4'-methoxy-4-biphenyl | —N(C$_2$H$_5$)$_2$ |

The second aspect of Category I relates to compounds having a substituted biphenyl $R^3$ unit providing a core scaffold with the general formula:

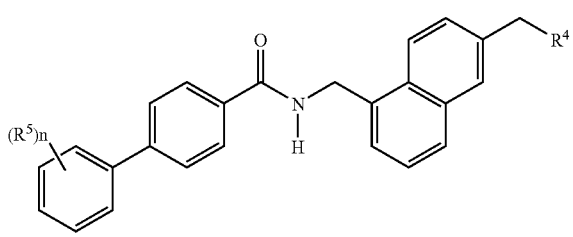

wherein $R^4$ units have the formula:

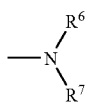

$R^6$ and $R^7$ units are taken together to from a heterocyclic or heteroaryl ring having from 3 to 8 atoms as further described herein below in Table II.

TABLE II

| No. | $R^3$ | $R^4$ |
|---|---|---|
| 66 | 4-biphenyl | aziridin-1-yl |
| 67 | 4-biphenyl | pyrrolidin-1-yl |
| 68 | 4-biphenyl | piperidin-1-yl |
| 69 | 4-biphenyl | piperazin-1-yl |
| 70 | 4-biphenyl | morpholin-4-yl |
| 71 | 4-biphenyl | azepan-1-yl |
| 72 | 3'-fluoro-4-biphenyl | aziridin-1-yl |
| 73 | 3'-fluoro-4-biphenyl | pyrrolidin-1-yl |
| 74 | 3'-fluoro-4-biphenyl | piperidin-1-yl |
| 75 | 3'-fluoro-4-biphenyl | piperazin-1-yl |
| 76 | 3'-fluoro-4-biphenyl | morpholin-4-yl |
| 77 | 3'-fluoro-4-biphenyl | azepan-1-yl |
| 78 | 3'-chloro-4-biphenyl | aziridin-1-yl |
| 79 | 3'-chloro-4-biphenyl | pyrrolidin-1-yl |
| 80 | 3'-chloro-4-biphenyl | piperidin-1-yl |
| 81 | 3'-chloro-4-biphenyl | piperazin-1-yl |
| 82 | 3'-chloro-4-biphenyl | morpholin-4-yl |
| 83 | 3'-chloro-4-biphenyl | azepan-1-yl |
| 84 | 3'-trifluoromethyl-4-biphenyl | aziridin-1-yl |
| 85 | 3'-trifluoromethyl-4-biphenyl | pyrrolidin-1-yl |
| 86 | 3'-trifluoromethyl-4-biphenyl | piperidin-1-yl |
| 87 | 3'-trifluoromethyl-4-biphenyl | piperazin-1-yl |
| 88 | 3'-trifluoromethyl-4-biphenyl | morpholin-4-yl |
| 89 | 3'-trifluoromethyl-4-biphenyl | azepan-1-yl |
| 90 | 3'-cyano-4-biphenyl | aziridin-1-yl |
| 91 | 3'-cyano-4-biphenyl | pyrrolidin-1-yl |
| 92 | 3'-cyano-4-biphenyl | piperidin-1-yl |
| 93 | 3'-cyano-4-biphenyl | piperazin-1-yl |
| 94 | 3'-cyano-4-biphenyl | morpholin-4-yl |
| 95 | 3'-cyano-4-biphenyl | azepan-1-yl |
| 96 | 3'-nitro-4-biphenyl | aziridin-1-yl |
| 97 | 3'-nitro-4-biphenyl | pyrrolidin-1-yl |
| 98 | 3'-nitro-4-biphenyl | piperidin-1-yl |
| 99 | 3'-nitro-4-biphenyl | piperazin-1-yl |
| 100 | 3'-nitro-4-biphenyl | morpholin-4-yl |
| 101 | 3'-nitro-4-biphenyl | azepan-1-yl |
| 102 | 3'-methoxy-4-biphenyl | aziridin-1-yl |
| 103 | 3'-methoxy-4-biphenyl | pyrrolidin-1-yl |
| 104 | 3'-methoxy-4-biphenyl | piperidin-1-yl |
| 105 | 3'-methoxy-4-biphenyl | piperazin-1-yl |
| 106 | 3'-methoxy-4-biphenyl | morpholin-4-yl |
| 107 | 3'-methoxy-4-biphenyl | azepan-1-yl |
| 108 | 4'-fluoro-4-biphenyl | aziridin-1-yl |
| 109 | 4'-fluoro-4-biphenyl | pyrrolidin-1-yl |
| 110 | 4'-fluoro-4-biphenyl | piperidin-1-yl |
| 111 | 4'-fluoro-4-biphenyl | piperazin-1-yl |
| 112 | 4'-fluoro-4-biphenyl | morpholin-4-yl |
| 113 | 4'-fluoro-4-biphenyl | azepan-1-yl |
| 114 | 4'-chloro-4-biphenyl | aziridin-1-yl |
| 115 | 4'-chloro-4-biphenyl | pyrrolidin-1-yl |
| 116 | 4'-chloro-4-biphenyl | piperidin-1-yl |
| 117 | 4'-chloro-4-biphenyl | piperazin-1-yl |
| 118 | 4'-chloro-4-biphenyl | morpholin-4-yl |
| 119 | 4'-chloro-4-biphenyl | azepan-1-yl |
| 120 | 4'-trifluoromethyl-4-biphenyl | aziridin-1-yl |
| 121 | 4'-trifluoromethyl-4-biphenyl | pyrrolidin-1-yl |
| 122 | 4'-trifluoromethyl-4-biphenyl | piperidin-1-yl |
| 123 | 4'-trifluoromethyl-4-biphenyl | piperazin-1-yl |
| 124 | 4'-trifluoromethyl-4-biphenyl | morpholin-4-yl |
| 125 | 4'-trifluoromethyl-4-biphenyl | azepan-1-yl |
| 126 | 4'-cyano-4-biphenyl | aziridin-1-yl |
| 127 | 4'-cyano-4-biphenyl | pyrrolidin-1-yl |
| 128 | 4'-cyano-4-biphenyl | piperidin-1-yl |
| 129 | 4'-cyano-4-biphenyl | piperazin-1-yl |
| 130 | 4'-cyano-4-biphenyl | morpholin-4-yl |
| 131 | 4'-cyano-4-biphenyl | azepan-1-yl |
| 132 | 4'-nitro-4-biphenyl | aziridin-1-yl |
| 133 | 4'-nitro-4-biphenyl | pyrrolidin-1-yl |
| 134 | 4'-nitro-4-biphenyl | piperidin-1-yl |
| 135 | 4'-nitro-4-biphenyl | piperazin-1-yl |
| 136 | 4'-nitro-4-biphenyl | morpholin-4-yl |
| 137 | 4'-nitro-4-biphenyl | azepan-1-yl |
| 138 | 4'-methoxy-4-biphenyl | aziridin-1-yl |
| 139 | 4'-methoxy-4-biphenyl | pyrrolidin-1-yl |
| 140 | 4'-methoxy-4-biphenyl | piperidin-1-yl |
| 141 | 4'-methoxy-4-biphenyl | piperazin-1-yl |
| 142 | 4'-methoxy-4-biphenyl | morpholin-4-yl |
| 143 | 4'-methoxy-4-biphenyl | azepan-1-yl |

The compounds which comprise the first and second aspect of Category I, wherein $R^2$ is equal to hydrogen, can be prepared by the procedure described herein below and outlined in Scheme I. However, the artisan can substitute other procedures which facilitate the achievement of higher yields, purity, or which utilize readily available starting materials that can be introduced into the procedures outlined herein below. For example is step (c), for the formation of intermediate 3, the artisan can substitute a different reagent when preparing the acid chloride, inter alia, thionyl chloride.

As is relates to the variations in $R^4$ for the first aspect of Category I compounds, in step (d) of Scheme I below, wherein intermediate 4 is prepared, the other aspects or iterations of this aspect of Category I can be prepared by the artisan substituting $H_3$, $NH_2CH_3$, $NH(CH_2CH_3)_2$, $NH(CH_3)(CH_2CH_3)$, $NH_2(CH_2CH_3)$, $NH_2[CH(CH_3)_2]$, and $NH[CH(CH_3)_2]_2$, as well as other $NHR^6R^7$ amines wherein $R^6$ and $R^7$ are each independently $C_1$-$C_8$ substituted or unsubstituted linear or branched hydrocarbyl units, for $NH(CH_3)_2$ in step (d). However, the conditions may be necessarily adjusted by the formulator using practices standard and known to the skilled artisan.

As it relates to compounds encompassed by the second aspect of Category I, wherein $R^6$ and $R^7$ can be taken together to form a heterocyclic ring having from 3 to 8 atoms, aziridine, pyrrolidine, piperidine, piperazine, 1H-azepine, and morpholine, for example, these rings can be substituted for $NH(CH_3)_2$ in step (d) of Scheme I herein below. However, the conditions may be necessarily adjusted by the formulator using practices standard and known to the skilled artisan.

Likewise, 4'-fluoro-biphenyl-4-carbonyl chloride is replaced with 4'-chloro-biphenyl-4-carbonyl chloride, 4'-trifluoromethyl-biphenyl-4-carbonyl chloride, and the like to affect the full range of R units under Category I, first and second aspects.

Scheme I

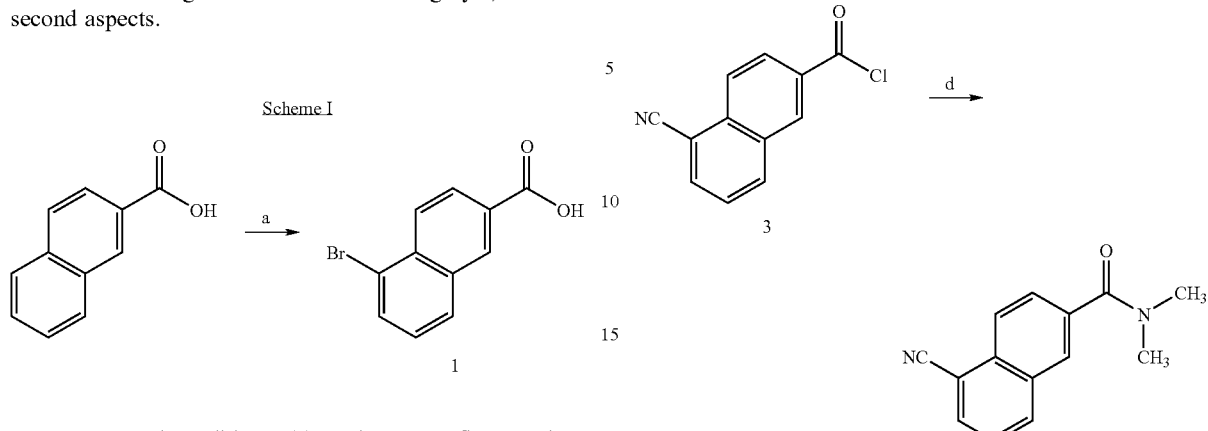

Reagents and conditions: (a) Br$_2$/AcOH; reflux, 0.5 hr.

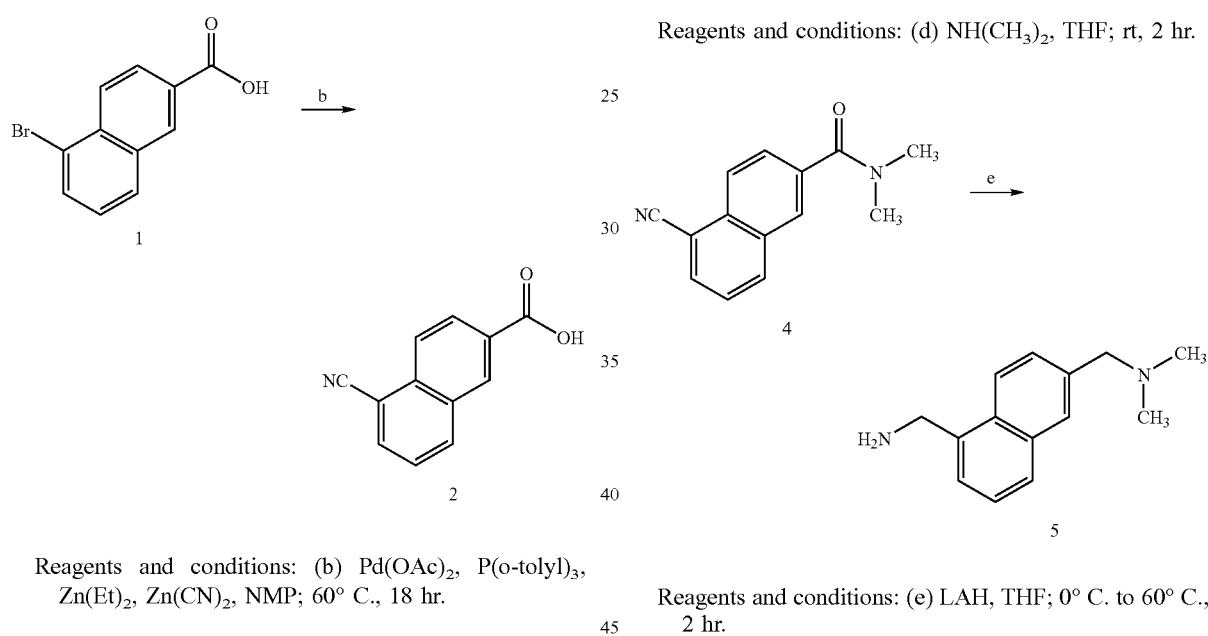

Reagents and conditions: (b) Pd(OAc)$_2$, P(o-tolyl)$_3$, Zn(Et)$_2$, Zn(CN)$_2$, NMP; 60° C., 18 hr.

Reagents and conditions: (c) (COCl)$_2$; rt, 0.5 hr.

Reagents and conditions: (d) NH(CH$_3$)$_2$, THF; rt, 2 hr.

Reagents and conditions: (e) LAH, THF; 0° C. to 60° C., 2 hr.

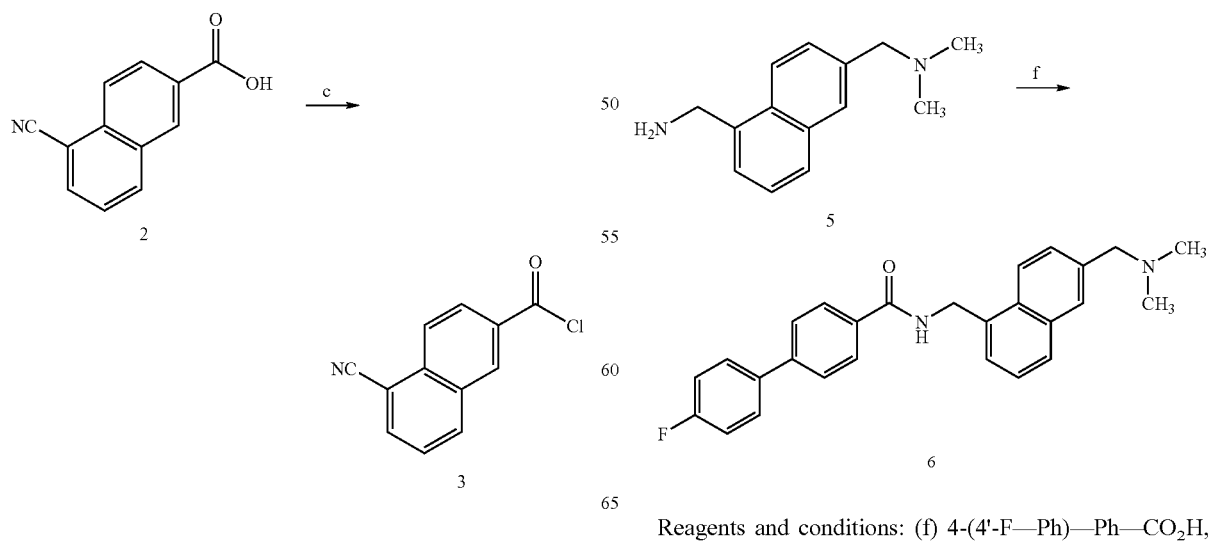

Reagents and conditions: (f) 4-(4'-F—Ph)—Ph—CO$_2$H, HOBt, EDCI, TEA, DMF; rt, 2 hr.

EXAMPLE 1

4'-Fluoro-biphenyl-4-carboxylic acid (6-dimethylaminomethyl-naphthalen-1-ylmethyl)-amide (6)

Preparation of 5-bromo-naphthalene-2-carboxylic acid (1): To a boiling solution of 2-naphthoic acid (10.00 g, 58.14 mmol) in acetic acid (50 mL) is added dropwise bromine (3 mL) containing iodine (0.25 g). After the addition is complete, the solution is refluxed for 0.5 hr. A white precipitate forms during cooling and is isolated by filtration, washed with acetic acid and then water. The solid is triturated in methanol (100 mL) and 7.01 g (53.4% yield) of the desired product is obtained as a white solid. m.p. 248-250° C. $^1$H NMR (300 MHz, CD$_3$OD): δ 8.94 (d, J=1.8 Hz, 1H), 8.52-8.42 (m, 3H), 8.27 (dd, J=1.8, 7.5 Hz, 1H), 7.79 (t, J=8.4 Hz, 1H).

Preparation of 5-cyano-naphthalene-2-carboxylic acid (2): A solution of Pd(OAc)$_2$ (0.012 g, 0.054 mmol) and tri-o-tolylphosphine (0.073 g, 0.240 mmol) in degassed N-methylpyrrolidone (2 mL) is heated at 60° C. for 30 minutes. A solution of 1.0 M diethylzinc in hexane (0.11 mL, 0.11 mmol) is then added and stirring is continued for additional 30 minutes. To this mixture is added a mixture of 5-bromo-naphthalene-2-carboxylic acid, 1, (0.135 g, 0.536 mmol) and Zn(CN)$_2$ (0.063 g, 0.536 mmol) in degassed N-methylpyrrolidone (2 mL). The resulting mixture is heated at 60° C. for 18 hrs. The reaction mixture is cooled and directly loaded to a prep-HPLC column eluting with CH$_3$CN—H$_2$O (0.1% TFA) to afford 0.085 g (80% yield) of the desired product as a white solid. m.p. 250° C. (dec.). $^1$H NMR (300 MHz, CDCl$_3$): δ 8.61 (s, 1H), 8.18 (m, 2H), 8.14 (d, J=8.7 Hz, 1H), 7.94 (d, J=7.2 Hz, 1H), 7.54 (t, J=8.4 Hz, 1H). $^{13}$C NMR (75 MHz, CDCl$_3$): δ 168.4, 134.9, 134.8, 134.5, 132.4, 131.9, 129.9, 128.5, 125.9, 125.5, 117.5, 110.2.

Preparation of 5-cyano-naphthalene-2-carboxylic acid chloride (3): To a suspension of 5-cyano-naphthalene-2-carboxylic acid, 2, (0.084 g, 0.426 mmol) in CH$_2$Cl$_2$ (2 mL) at room temperature containing 1 drop of DMF is added oxalyl chloride (0.074 mL). Once the solution is homogeneous, the solution is concentrated in vacuo and the crude product is used without further purification.

Preparation of 5-cyano-naphthalene-2-carboxylic acid dimethylamide (4): The crude product obtained above is dissolved in CH$_2$Cl$_2$ (2 mL) and 2.0 M Me$_2$NH in THF (0.64 mL, 3.0 eq.) is added. The resulting solution is stirred at room temperature for 2 hours. The reaction mixture is washed with saturated NaHCO$_3$, dried over anhydrous MgSO$_4$ and evaporated to afford 0.095 g of the desired product as an off-white solid. The product is used for the next step without further purification. $^1$H NMR (300 MHz, CDCl$_3$): δ 8.20 (d, J=9.0 Hz, 1H), 8.06 (d, J=8.4 Hz, 1H), 7.96 (s, 1H), 7.90 (d, J=7.2 Hz, 1H), 7.68 (dd, J=1.2, 9.0 Hz, 1H), 7.53 (t, J=8.1 Hz, 1H), 3.12 (s, 3H), 2.98 (s, 3H). $^{13}$C NMR (75 MHz, CDCl$_3$): δ 170.7, 135.7, 133.9, 133.8, 132.6, 127.7, 127.3, 126.1, 125.7, 123.7, 117.7, 110.4, 39.8, 35.7.

Preparation of C-(6-dimethylaminomethyl-naphthalen-1-yl)-methylamine di-TFA salt (5): To a 0° C. solution of 5-cyano-naphthalene-2-carboxylic acid dimethylamide, 4, (0.095 g, 424 mmol) in anhydrous THF (5 mL) is added LAH (0.85 mL, 1M in THF, 2 eq.). After the addition is complete, the resulting solution is heated to 60° C. for 2 hours. The solution is cooled then the reaction quenched with 1N NaOH (several drops) and the white precipitate which forms is removed by filtration. The filtrate is concentrated in vacuo and the crude residue is purified by prep HPLC eluting with CH$_3$CN:H$_2$O (0.1% TFA) to afford 0.188 g of the desired product as the di-TFA salt. $^1$H NMR (300 MHz, CD$_3$OD): δ 8.30 (d, J=9.0 Hz, 1H), 8.24 (d, J=1.8 Hz, 1H), 8.09 (d, J=7.8 Hz, 1H), 7.87 (dd, J=1.8, 8.7 Hz, 1H), 7.78 (d, J=6.6 Hz, 1H), 7.66 (d, J=8.4 Hz, 1H), 4.70 (s, 2H), 4.60, (s, 2H), 2.72 (s, 6H). LRMS: 214.98 (M+1), 169.89 (M+1-Me$_2$NH).

Preparation of 4'-fluoro-biphenyl-4-carboxylic acid (6-dimethylaminomethyl-naphthalen-1-ylmethyl)-amide (6): A solution of C-(6-dimethylaminomethyl-naphthalen-1-yl)-methylamine di-TFA salt, 5, (0.180 g, 0.407 mmol), 4'-fluoro-biphenyl-4-carboxylic acid (0.088 g, 1 eq.), 1-hydroxybenzotriazole (0.066 g, 1.2 eq.), 1-(3-dimethylaminopropyl)-3-ethylcarbo-diimide (0.093 g, 1.2 eq.) and triethylamine (0.17 mL, 3 eq.) in DMF (5 mL) is stirred at room temperature for 2 hours. The reaction solution is concentrated in vacuo and then purified by prep HPLC eluting with CH$_3$CN:H$_2$O (0.1% TFA) to afford the desired product as the TFA salt which is treated with HCl to afford 50 mg (30% yield) of the desired product as the HCl salt in the form of a light yellow solid. $^1$H NMR (300 MHz, CD$_3$OD): δ 8.39 (d, J=9.0 Hz, 1H), 8.12 (s, 1H), 8.01-7.95 (m, 3H), 7.76-7.58 (m, 8H), 7.23 (t, J=9.0 Hz, 1H), 5.14 (s, 2H), 4.54 (s, 2H), 2.94 (s, 6H). $^{13}$C NMR (75 MHz, CD$_3$OD): δ 169.6, 165.2 (d, J=240 Hz), 163.5, 144.7, 137.5, 135.7, 135.1, 134.1, 133.2, 133.0, 130.1 (d, J=7.5 Hz), 129.5, 129.1, 128.6, 128.5, 128.0, 127.8, 126.2, 116.8 (d, J=22 Hz), 116.7, 62.3, 43.1, 42.5. $^{19}$F NMR (282 MHz, CD$_3$OD): δ 45.8. Mass Spec.: Calcd.: 413.2029; found HRMS: 413.2019; Formula: C$_{27}$H$_{25}$FN$_2$O+H, found LRMS: 413.27.

4'-Trifluoromethyl-biphenyl-4-carboxylic acid (6-diethylaminomethyl-naphthalen-1-ylmethyl)-amide: $^1$H NMR (300 MHz, CD$_3$OD): δ 8.24 (d, J=8.7 Hz, 1H), 8.15 (s, 1H), 8.03 (s, 1H), 7.93 (s, 1H), 7.77 (d, J=6.8 Hz, 1H), 7.72-7.67 (m, 8H), 7.62 (d, J=7.2 Hz, 1H), 4.66 (s, 2H), 4.58 (s, 2H), 3.51 (m, 4H), 2.08 (m, 6H). $^{13}$C NMR (75 MHz, CD$_3$OD) δ 170.0, 166.4, 163.2, 146.3, 138.0, 135.6, 132.9, 131.8, 131.1, 130.7, 130.5, 130.4, 129.6, 128.3, 128.2, 128.2, 125.7, 117.3, 117.0, 59.5, 55.4, 41.5, 24.3. LRMS: 490.78 (M+1).

4'-Fluoro-biphenyl-4-carboxylic acid (6-diethylaminomethyl-naphthalen-1-ylmethyl)-amide: $^1$H NMR (300 MHz, CD$_3$OD): δ 8.22 (d, J=8.7 Hz, 1H), 8.14 (s, 1H), 7.95 (d, J=8.3 Hz, 1H), 7.87-7.75 (m, 4H), 7.64 (s, 1H), 7.61-7.48 (m, 6H), 4.57 (s, 2H), 4.47 (s, 2H), 3.19 (q, J=7.2 Hz, 4H), 1.27 (t, J=7.6 Hz, 6H). $^{13}$C NMR (75 MHz, CD$_3$OD) δ 170.1, 164.3 (d, J=243 Hz), 146.2, 136.7, 135.5, 133.6, 133.0, 132.6, 131.7, 131.2, 130.9, 130.6 (d, J=8 Hz), 130.2, 129.5, 128.7, 128.4, 128.1, 125.7, 117.1 (d, J=22 Hz), 64.9, 57.4, 41.5, 9.5. LRMS: 453.3 (M+1).

3'-Trifluoromethyl-biphenyl-4-carboxylic acid (6-diethylaminomethyl-naphthalen-1-ylmethyl)-amide: $^1$H NMR (300 MHz, CD$_3$OD): δ 8.18 (d, J=8.7 Hz, 1H), 7.98 (s, 1H), 7.90-7.85 (m, 3H), 7.77-7.75 (m, 4H), 7.63-7.49 (m, 3H), 7.44-7.39 (m, 2H), 5.19 (s, 2H), 4.37 (s, 2H), 3.28 (q, J=7.1 Hz, 4H), 1.17 (t, J=7.1 Hz, 6H). $^{13}$C NMR (75 MHz, CD$_3$OD) δ 170.9, 163.3, 144.3, 142.5, 136.0, 135.5, 133.4, 132.3, 131.5, 129.9, 129.8, 129.3, 128.8, 128.7, 128.6, 128.2, 126.4, 125.1, 120.5, 116.6, 112.7, 65.5, 57.60, 42.94, 9.44. LRMS: 490.8 (M+1).

Biphenyl-4-carboxylic acid (6-diethylaminomethyl-naphthalen-1-ylmethyl)-amide:
$^1$H NMR (300 MHz, CD$_3$OD): δ 8.35 (d, J=8.6 Hz, 1H), 8.10 (s, 1H), 7.95-7.91 (m, 3H), 7.73-7.69 (m, 2H), 7.67-7.63 (m, 4H), 7.58 (d, J=7.9 Hz, 1H), 7.48-7.43 (m, 2H), 7.38 (m, 1H), 5.10 (s, 2H), 4.51 (s, 2H), 3.24 (q, J=7.2 Hz, 4H), 1.35 (t, J=7.2 Hz, 6H). $^{13}$C NMR (75 MHz, CD$_3$OD) δ 169.9, 146.2, 141.5, 136.1, 135.6, 134.5, 133.4, 133.3, 130.4, 129.8, 129.5, 129.4, 129.0, 128.9, 128.7, 128.5, 128.4, 128.2, 126.6, 63.2, 57.6, 42.9, 9.4. LRMS: 422.8 (M+1).

4'-Fluoro-biphenyl-4-carboxylic acid (6-piperidin-1-ylmethyl-naphthalen-1-ylmethyl)-amide: $^1$H NMR (300 MHz, CD$_3$OD): δ 8.37 (d, J=8.8 Hz, 1H), 8.09 (s, 1H), 7.97 (m, 3H), 7.72-7.56 (m, 6H), 7.57 (d, J=7.8 Hz, 1H), 7.21 (t, J=8.8 Hz, 2H), 5.12 (s, 2H), 4.48 (s, 2H), 3.35 (m, 4H), 1.93 (m, 2H), 1.83-1.71 (m, 4H). $^{13}$C NMR (75 MHz, CD$_3$OD) δ 166.4, 164.4 (d, J=246 Hz), 145.1, 137.9, 136.0, 135.5, 134.5, 133.7, 133.5, 130.5 (d, J=8 Hz), 130.4, 129.8, 129.5, 129.3, 128.9, 128.4, 128.1, 126.4, 117.1 (d, J=22 Hz), 62.12, 54.48, 42.94, 24.48, 23.10. LRMS: 503.3 (M+1); 453.3 (M+1).

4'-Trifluoromethyl-biphenyl-4-carboxylic acid (6-piperidin-1-ylmethyl-naphthalen-1-ylmethyl)-amide: $^1$H NMR (300 MHz, CD$_3$OD): δ 8.36 (d, J=8.7 Hz, 1H), 8.09 (s, 1H), 8.01-7.97 (m, 2H), 7.92 (d, J=8.0 Hz, 1H), 7.89 (m, 2H), 7.82 (s, 1H), 7.79 (m, 2H), 7.76 (s, 1H), 7.69-7.67 (m, 2H), 7.60 (d, J=8.0 Hz, 1H), 5.15 (s, 2H), 4.48 (s, 2H), 3.30-3.10 (m, 4H), 1.95 (m, 6H). $^{13}$C NMR (75 MHz, CD$_3$OD) δ 171.3, 165.3, 163.6, 146.8, 139.0, 136.1, 135.5, 133.7, 129.9, 129.6, 129.2, 128.8, 128.2, 127.3, 126.5, 126.1, 125.9, 116.7, 116.2, 62.2, 54.5, 42.9, 24.5, 23.1; LRMS: (M+1): 503.0.

3'-Trifluoromethyl-biphenyl-4-carboxylic acid (6-piperidin-1-ylmethyl-naphthalen-1-ylmethyl)-amide: $^1$H NMR (300 MHz, CD$_3$OD): δ 8.25 (d, J=8.7 Hz, 1H), 8.02 (s, 1H), 7.95 (m, 2H), 7.84-7.78 (m, 3H), 7.64-7.57 (m, 6H), 7.48 (d, J=9.6 Hz, 1H), 5.03 (s, 2H), 4.37 (s, 2H), 3.10 (m, 4H), 1.91 (m, 6H). $^{13}$C NMR (75 MHz, CD$_3$OD) δ 169.8, 144.2, 142.5, 136.0, 135.4, 133.7, 133.4, 132.2, 131.3, 130.4, 129.9, 129.7, 129.7, 129.5, 128.8, 128.6, 128.2, 128.1, 126.3, 125.0, 125.0, 62.0, 54.4, 45.8, 43.0, 24.4. LRMS: 502.8 (M+1).

Biphenyl-4-carboxylic acid (6-piperidin-1-ylmethyl-naphthalen-1-ylmethyl)-amide: $^1$H NMR (300 MHz, CD$_3$OD): δ 8.24 (d, J=8.7 Hz, 1H), 7.94 (s, 1H), 7.87-7.77 (m, 3H), 7.65-7.59 (m, 2H), 7.59-7.51 (m, 4H), 7.74 (d, J=8.0 Hz, 1H), 7.4-7.31 (m, 2H), 7.27 (d, J=7.2 Hz, 1H), 5.01 (s, 2H), 4.36 (s, 2H), 3.42 (m, 2H), 2.94 (m, 2H), 1.87-1.60 (m, 6H). $^{13}$C NMR (75 MHz, CD$_3$OD) δ 170.1, 146.1, 141.4, 136.0, 135.5, 134.5, 133.7, 132.5, 130.4, 129.9, 129.5, 129.5, 129.0, 128.7, 128.5, 128.4, 128.2, 127.9, 126.5, 61.7, 54.5, 42.9, 24.5, 23.1. LRMS: 434.9 (M+1).

4'-Trifluoromethyl-biphenyl-4-carboxylic acid (6-pyrrolidin-1-ylmethyl-naphthalen-1-ylmethyl)-amide: $^1$H NMR (300 MHz, CD$_3$OD): $^1$H NMR (300 MHz, CD$_3$OD): δ 8.25 (d, J=8.7 Hz, 1H), 7.98 (s, 1H), 7.91-7.84 (m, 2H), 7.80 (d, J=8.1 Hz, 1H), 0.78-7.72 (m, 2H), 7.71-7.62 (m, 4H), 7.59-7.52 (m, 2H), 7.46 (d, J=8.0 Hz, 1H), 5.00 (s, 2H), 4.45 (s, 2H), 3.41 (m, 2H), 3.16 (m, 2H), 1.97 (m, 4H). $^{13}$C NMR (75 MHz, CD$_3$OD) δ 169.9, 145.4, 144.4, 136.0, 135.6, 133.4, 132.7, 131.2, 130.3, 129.9, 129.6, 129.2, 128.9, 128.8, 128.7, 128.6, 128.1, 126.7, 126.6, 59.7, 55.4, 43.0, 24.2. LRMS: 489.33 (M+1).

4'-Fluoro-biphenyl-4-carboxylic acid (6-pyrrolidin-1-ylmethyl-naphthalen-1-ylmethyl)-methyl-amide: $^1$H NMR (300 MHz, CD$_3$OD): δ 8.23 (d, J=8.7 Hz, 1H), 7.97 (s, 1H), 7.87-7.76 (m, 3H), 7.63-7.52 (m, 6H), 7.45 (d, J=7.9 Hz, 1H), 7.14-7.03 (m, 2H), 4.99 (s, 2H), 4.44 (s, 2H), 3.40 (m, 2H), 3.15 (m, 2H), 2.15-1.90 (m, 4H). $^{13}$C NMR (75 MHz, CD$_3$OD) δ 170.0, 164.8 (d, J=245 Hz), 145.1, 136.1, 135.6, 134.5, 133.4, 132.6, 130.5, 130.4 (d, J=8 Hz), 129.8, 129.5, 128.8, 128.6, 128.4, 128.1, 126.5, 117.3, 117.0 (d, J=22 Hz), 59.7, 55.4, 42.9, 24.2. LRMS: 439.35 (M+1).

3'-Trifluoromethyl-biphenyl-4-carboxylic acid (6-pyrrolidin-1-ylmethyl-naphthalen-1-ylmethyl)-amide: $^1$H NMR (300 MHz, CD$_3$OD): δ 8.25 (d, J=8.6 Hz, 1H), 8.02 (s, 1H), 7.94 (m, 2H), 7.84-7.79 (m, 3H), 7.66-7.58 (m, 6H), 7.48 (d, J=7.6 Hz, 1H), 5.03 (s, 2H), 4.47 (s, 2H), 3.40-3.20 (m, 4H), 2.05 (m, 4H). $^{13}$C NMR (75 MHz, CD$_3$OD) δ 170.0, 144.3, 142.5, 135.9, 135.5, 135.4, 133.3, 132.7, 132.2, 131.3, 129.9, 129.7, 128.7, 128.6, 128.1, 126.4, 126.1, 125.0, 125.0, 120.6, 116.4, 59.6, 55.2, 43.0, 24.2. LRMS: 489.37 (M+1).

Biphenyl-4-carboxylic acid (6-pyrrolidin-1-ylmethyl-naphthalen-1-ylmethyl)-amide: $^1$H NMR (300 MHz, CD$_3$OD): δ 8.11 (d, J=8.6 Hz, 1H), 7.88 (s, 1H), 7.81-7.76 (m, 2H), 7.71 (d, J=8.0 Hz, 1H), 7.55-7.42 (m, 6H), 7.35 (d, J=7.7 Hz, 1H), 7.29-7.16 (m, 3H), 4.90 (s, 2H), 4.32 (s, 2H), 3.31-3.10 (m, 4H), 1.92 (m, 4H). $^{13}$C NMR (75 MHz, CD$_3$OD) δ 170.1, 146.0, 141.4, 136.0, 135.5, 134.5, 133.3, 132.6, 130.4, 129.8, 129.5, 129.5, 128.7, 128.6, 128.5, 128.4, 128.1, 127.9, 126.4, 59.6, 59.2, 42.9, 24.2. LRMS: 421.39 (M+1).

Other compounds which comprise the first aspect of Category I that are not specifically exemplified herein include the following:

4'-Fluoro-biphenyl-4-carboxylic acid (6-aminomethyl-naphthalen-1-ylmethyl)-amide;

4'-Chloro-biphenyl-4-carboxylic acid (6-aminomethyl-naphthalen-1-ylmethyl)-amide;

4'-Trifluoromethyl-biphenyl-4-carboxylic acid (6-aminomethyl-naphthalen-1-ylmethyl)-amide;

4'-Cyano-biphenyl-4-carboxylic acid (6-aminomethyl-naphthalen-1-ylmethyl)-amide;

4'-Nitro-biphenyl-4-carboxylic acid (6-aminomethyl-naphthalen-1-ylmethyl)-amide;

4'-Methyl-biphenyl-4-carboxylic acid (6-aminomethyl-naphthalen-1-ylmethyl)-amide;

4'-Methoxy-biphenyl-4-carboxylic acid (6-aminomethyl-naphthalen-1-ylmethyl)-amide;

4'-Chloro-biphenyl-4-carboxylic acid (6-dimethylaminomethyl-naphthalen-1-ylmethyl)-amide;

4'-Trifluoromethyl-biphenyl-4-carboxylic acid (6-dimethylaminomethyl-naphthalen-1-ylmethyl)-amide;

4'-Cyano-biphenyl-4-carboxylic acid (6-dimethylaminomethyl-naphthalen-1-ylmethyl)-amide;

4'-Nitro-biphenyl-4-carboxylic acid (6-dimethylaminomethyl-naphthalen-1-ylmethyl)-amide;

4'-Methyl-biphenyl-4-carboxylic acid (6-dimethylaminomethyl-naphthalen-1-ylmethyl)-amide;

4'-Methoxy-biphenyl-4-carboxylic acid (6-dimethylaminomethyl-naphthalen-1-ylmethyl)-amide;

4'-Chloro-biphenyl-4-carboxylic acid (6-diethylaminomethyl-naphthalen-1-ylmethyl)-amide;

4'-Cyano-biphenyl-4-carboxylic acid (6-diethylaminomethyl-naphthalen-1-ylmethyl)-amide;

4'-Nitro-biphenyl-4-carboxylic acid (6-diethylaminomethyl-naphthalen-1-ylmethyl)-amide;

4'-Methyl-biphenyl-4-carboxylic acid (6-diethylaminomethyl-naphthalen-1-ylmethyl)-amide;

4'-Methoxy-biphenyl-4-carboxylic acid (6-diethylaminomethyl-naphthalen-1-ylmethyl)-amide;

4'-Fluoro-biphenyl-4-carboxylic acid (6-methylaminomethyl-naphthalen-1-ylmethyl)-amide;

4'-Chloro-biphenyl-4-carboxylic acid (6-methylaminomethyl-naphthalen-1-ylmethyl)-amide;

4'-Trifluoromethyl-biphenyl-4-carboxylic acid (6-methylaminomethyl-naphthalen-1-ylmethyl)-amide;

4'-Cyano-biphenyl-4-carboxylic acid (6-methylaminomethyl-naphthalen-1-ylmethyl)-amide;
4'-Nitro-biphenyl-4-carboxylic acid (6-methylaminomethyl-naphthalen-1-ylmethyl)-amide;
4'-Methyl-biphenyl-4-carboxylic acid (6-methylaminomethyl-naphthalen-1-ylmethyl)-amide;
4'-Methoxy-biphenyl-4-carboxylic acid (6-methylaminomethyl-naphthalen-1-ylmethyl)-amide;
4'-Fluoro-biphenyl-4-carboxylic acid (6-ethylaminomethyl-naphthalen-1-ylmethyl)-amide;
4'-Chloro-biphenyl-4-carboxylic acid (6-ethylaminomethyl-naphthalen-1-ylmethyl)-amide;
4'-Trifluoromethyl-biphenyl-4-carboxylic acid (6-ethylaminomethyl-naphthalen-1-ylmethyl)-amide;
4'-Cyano-biphenyl-4-carboxylic acid (6-ethylaminomethyl-naphthalen-1-ylmethyl)-amide;
4'-Nitro-biphenyl-4-carboxylic acid (6-ethylaminomethyl-naphthalen-1-ylmethyl)-amide;
4'-Methyl-biphenyl-4-carboxylic acid (6-ethylaminomethyl-naphthalen-1-ylmethyl)-amide; and
4'-Methoxy-biphenyl-4-carboxylic acid (6-ethylaminomethyl-naphthalen-1-ylmethyl)-amide.

Further compounds according to Category I wherein $R^6$ and $R^7$ are taken together to form a ring comprising 3 to 8 atoms:
4'-Chloro-biphenyl-4-carboxylic acid (6-pyrrolidin-1-ylmethyl-naphthalen-1-ylmethyl)-amide;
4'-Cyano-biphenyl-4-carboxylic acid (6-pyrrolidin-1-ylmethyl-naphthalen-1-ylmethyl)-amide;
4'-Nitro-biphenyl-4-carboxylic acid (6-pyrrolidin-1-ylmethyl-naphthalen-1-ylmethyl)-amide;
4'-Methyl-biphenyl-4-carboxylic acid (6-pyrrolidin-1-ylmethyl-naphthalen-1-ylmethyl)-amide;
4'-Methoxy-biphenyl-4-carboxylic acid (6-pyrrolidin-1-ylmethyl-naphthalen-1-ylmethyl)-amide;
4'-Chloro-biphenyl-4-carboxylic acid (6-piperidin-1-ylmethyl-naphthalen-1-ylmethyl)-amide;
4'-Cyano-biphenyl-4-carboxylic acid (6-piperidin-1-ylmethyl-naphthalen-1-ylmethyl)-amide;
4'-Nitro-biphenyl-4-carboxylic acid (6-piperidin-1-ylmethyl-naphthalen-1-ylmethyl)-amide;
4'-Methyl-biphenyl-4-carboxylic acid (6-piperidin-1-ylmethyl-naphthalen-1-ylmethyl)-amide;
4'-Methoxy-biphenyl-4-carboxylic acid (6-piperidin-1-ylmethyl-naphthalen-1-ylmethyl)-amide;
4'-Fluoro-biphenyl-4-carboxylic acid (6-piperazin-1-ylmethyl-naphthalen-1-ylmethyl)-amide;
4'-Chloro-biphenyl-4-carboxylic acid (6-piperazin-1-ylmethyl-naphthalen-1-ylmethyl)-amide;
4'-Trifluoromethyl-biphenyl-4-carboxylic acid (6-piperazin-1-ylmethyl-naphthalen-1-ylmethyl)-amide;
4'-Cyano-biphenyl-4-carboxylic acid (6-piperazin-1-ylmethyl-naphthalen-1-ylmethyl)-amide;
4'-Nitro-biphenyl-4-carboxylic acid (6-piperazin-1-ylmethyl-naphthalen-1-ylmethyl)-amide;
4'-Methyl-biphenyl-4-carboxylic acid (6-piperazin-1-ylmethyl-naphthalen-1-ylmethyl)-amide;
4'-Methoxy-biphenyl-4-carboxylic acid (6-piperazin-1-ylmethyl-naphthalen-1-ylmethyl)-amide;
4'-Fluoro-biphenyl-4-carboxylic acid (6-aziridin-1-ylmethyl-naphthalen-1-ylmethyl)-amide;
4'-Chloro-biphenyl-4-carboxylic acid (6-aziridin-1-ylmethyl-naphthalen-1-ylmethyl)-amide;
4'-Trifluoromethyl-biphenyl-4-carboxylic acid (6-aziridin-1-ylmethyl-naphthalen-1-ylmethyl)-amide;
4'-Cyano-biphenyl-4-carboxylic acid (6-aziridin-1-ylmethyl-naphthalen-1-ylmethyl)-amide;
4'-Nitro-biphenyl-4-carboxylic acid (6-aziridin-1-ylmethyl-naphthalen-1-ylmethyl)-amide;
4'-Methyl-biphenyl-4-carboxylic acid (6-aziridin-1-ylmethyl-naphthalen-1-ylmethyl)-amide;
4'-Methoxy-biphenyl-4-carboxylic acid (6-aziridin-1-ylmethyl-naphthalen-1-ylmethyl)-amide;
4'-Fluoro-biphenyl-4-carboxylic acid (6-morpholin-4-ylmethyl-naphthalen-1-ylmethyl)-amide;
4'-Chloro-biphenyl-4-carboxylic acid (6-morpholin-4-ylmethyl-naphthalen-1-ylmethyl)-amide;
4'-Trifluoromethyl-biphenyl-4-carboxylic acid (6-morpholin-4-ylmethyl-naphthalen-1-ylmethyl)-amide;
4'-Cyano-biphenyl-4-carboxylic acid (6-morpholin-4-ylmethyl-naphthalen-1-ylmethyl)-amide;
4'-Nitro-biphenyl-4-carboxylic acid (6-morpholin-4-ylmethyl-naphthalen-1-ylmethyl)-amide;
4'-Methyl-biphenyl-4-carboxylic acid (6-morpholin-4-ylmethyl-naphthalen-1-ylmethyl)-amide; and
4'-Methoxy-biphenyl-4-carboxylic acid (6-morpholin-4-ylmethyl-naphthalen-1-ylmethyl)-amide.

However, other compounds according to Category I of the present invention can be prepared by the method of Scheme I or by modifications made to Scheme I which are well understood by the artisan of ordinary skill.

Category II of the present invention relates to compounds with a core scaffold having the formula:

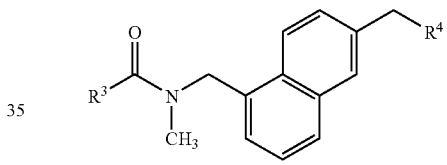

and a substituted biphenyl $R^3$ unit providing a core scaffold with the general formula:

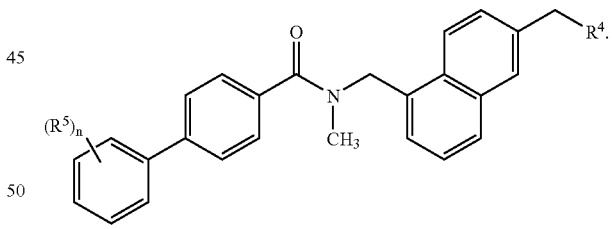

The first aspect of Category II relates to $R^4$ units having the formula:

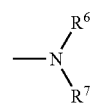

wherein $R^6$ and $R^7$ units each independently comprise hydrogen or $C_1$-$C_8$ substituted or unsubstituted linear or branched hydrocarbyl as further described herein below in Table III

TABLE III

| No. | R³ | R⁴ |
|---|---|---|
| 144 | 4-biphenyl | —NH₂ |
| 145 | 4-biphenyl | —NHCH₃ |
| 146 | 4-biphenyl | —N(CH₃)₂ |
| 147 | 4-biphenyl | —NH(C₂H₅) |
| 148 | 4-biphenyl | —N(C₂H₅)₂ |
| 149 | 3'-fluoro-4-biphenyl | —NH₂ |
| 150 | 3'-fluoro-4-biphenyl | —NHCH₃ |
| 151 | 3'-fluoro-4-biphenyl | —N(CH₃)₂ |
| 152 | 3'-fluoro-4-biphenyl | —NH(C₂H₅) |
| 153 | 3'-fluoro-4-biphenyl | —N(C₂H₅)₂ |
| 154 | 3'-chloro-4-biphenyl | —NH₂ |
| 155 | 3'-chloro-4-biphenyl | —NHCH₃ |
| 156 | 3'-chloro-4-biphenyl | —N(CH₃)₂ |
| 157 | 3'-chloro-4-biphenyl | —NH(C₂H₅) |
| 158 | 3'-chloro-4-biphenyl | —N(C₂H₅)₂ |
| 159 | 3'-trifluoromethyl-4-biphenyl | —NH₂ |
| 160 | 3'-trifluoromethyl-4-biphenyl | —NHCH₃ |
| 161 | 3'-trifluoromethyl-4-biphenyl | —N(CH₃)₂ |
| 162 | 3'-trifluoromethyl-4-biphenyl | —NH(C₂H₅) |
| 163 | 3'-trifluoromethyl-4-biphenyl | —N(C₂H₅)₂ |
| 164 | 3'-cyano-4-biphenyl | —NH₂ |
| 165 | 3'-cyano-4-biphenyl | —NHCH₃ |
| 166 | 3'-cyano-4-biphenyl | —N(CH₃)₂ |
| 167 | 3'-cyano-4-biphenyl | —NH(C₂H₅) |
| 168 | 3'-cyano-4-biphenyl | —N(C₂H₅)₂ |
| 169 | 3'-nitro-4-biphenyl | —NH₂ |
| 170 | 3'-nitro-4-biphenyl | —NHCH₃ |
| 171 | 3'-nitro-4-biphenyl | —N(CH₃)₂ |
| 172 | 3'-nitro-4-biphenyl | —NH(C₂H₅) |
| 173 | 3'-nitro-4-biphenyl | —N(C₂H₅)₂ |
| 174 | 3'-methoxy-4-biphenyl | —NH₂ |
| 175 | 3'-methoxy-4-biphenyl | —NHCH₃ |
| 176 | 3'-methoxy-4-biphenyl | —N(CH₃)₂ |
| 177 | 3'-methoxy-4-biphenyl | —NH(C₂H₅) |
| 178 | 3'-methoxy-4-biphenyl | —N(C₂H₅)₂ |
| 179 | 4'-fluoro-4-biphenyl | —NH₂ |
| 180 | 4'-fluoro-4-biphenyl | —NHCH₃ |
| 181 | 4'-fluoro-4-biphenyl | —N(CH₃)₂ |
| 182 | 4'-fluoro-4-biphenyl | —NH(C₂H₅) |
| 183 | 4'-fluoro-4-biphenyl | —N(C₂H₅)₂ |
| 184 | 4'-chloro-4-biphenyl | —NH₂ |
| 185 | 4'-chloro-4-biphenyl | —NHCH₃ |
| 186 | 4'-chloro-4-biphenyl | —N(CH₃)₂ |
| 187 | 4'-chloro-4-biphenyl | —NH(C₂H₅) |
| 188 | 4'-chloro-4-biphenyl | —N(C₂H₅)₂ |
| 189 | 4'-trifluoromethyl-4-biphenyl | —NH₂ |
| 190 | 4'-trifluoromethyl-4-biphenyl | —NHCH₃ |
| 191 | 4'-trifluoromethyl-4-biphenyl | —N(CH₃)₂ |
| 192 | 4'-trifluoromethyl-4-biphenyl | —NH(C₂H₅) |
| 193 | 4'-trifluoromethyl-4-biphenyl | —N(C₂H₅)₂ |
| 194 | 4'-cyano-4-biphenyl | —NH₂ |
| 195 | 4'-cyano-4-biphenyl | —NHCH₃ |
| 196 | 4'-cyano-4-biphenyl | —N(CH₃)₂ |
| 197 | 4'-cyano-4-biphenyl | —NH(C₂H₅) |
| 198 | 4'-cyano-4-biphenyl | —N(C₂H₅)₂ |
| 199 | 4'-nitro-4-biphenyl | —NH₂ |
| 200 | 4'-nitro-4-biphenyl | —NHCH₃ |
| 201 | 4'-nitro-4-biphenyl | —N(CH₃)₂ |
| 202 | 4'-nitro-4-biphenyl | —NH(C₂H₅) |
| 203 | 4'-nitro-4-biphenyl | —N(C₂H₅)₂ |
| 204 | 4'-methoxy-4-biphenyl | —NH₂ |
| 205 | 4'-methoxy-4-biphenyl | —NHCH₃ |
| 206 | 4'-methoxy-4-biphenyl | —N(CH₃)₂ |
| 207 | 4'-methoxy-4-biphenyl | —NH(C₂H₅) |
| 208 | 4'-methoxy-4-biphenyl | —N(C₂H₅)₂ |

The second aspect of Category II relates to compounds having a substituted biphenyl R³ with the general formula:

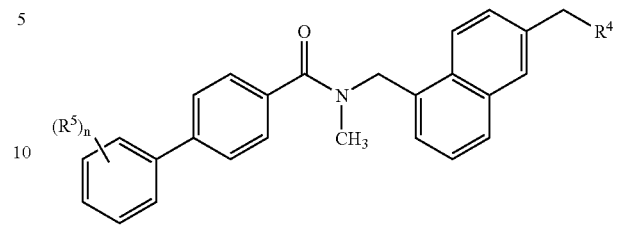

wherein R⁴ units have the formula:

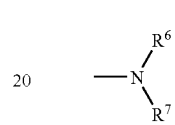

R⁶ and R⁷ units are taken together to from a heterocyclic or heteroaryl ring having from 3 to 8 atoms as further described herein below in Table IV

TABLE IV

| No. | R³ | R⁴ |
|---|---|---|
| 209 | 4-biphenyl | aziridin-1-yl |
| 210 | 4-biphenyl | pyrrolidin-1-yl |
| 211 | 4-biphenyl | piperidin-1-yl |
| 212 | 4-biphenyl | piperazin-1-yl |
| 213 | 4-biphenyl | morpholin-4-yl |
| 214 | 4-biphenyl | azepan-1-yl |
| 215 | 3'-fluoro-4-biphenyl | aziridin-1-yl |
| 216 | 3'-fluoro-4-biphenyl | pyrrolidin-1-yl |
| 217 | 3'-fluoro-4-biphenyl | piperidin-1-yl |
| 218 | 3'-fluoro-4-biphenyl | piperazin-1-yl |
| 219 | 3'-fluoro-4-biphenyl | morpholin-4-yl |
| 220 | 3'-fluoro-4-biphenyl | azepan-1-yl |
| 221 | 3'-chloro-4-biphenyl | aziridin-1-yl |
| 222 | 3'-chloro-4-biphenyl | pyrrolidin-1-yl |
| 223 | 3'-chloro-4-biphenyl | piperidin-1-yl |
| 224 | 3'-chloro-4-biphenyl | piperazin-1-yl |
| 225 | 3'-chloro-4-biphenyl | morpholin-4-yl |
| 226 | 3'-chloro-4-biphenyl | azepan-1-yl |
| 227 | 3'-trifluoromethyl-4-biphenyl | aziridin-1-yl |
| 228 | 3'-trifluoromethyl-4-biphenyl | pyrrolidin-1-yl |
| 229 | 3'-trifluoromethyl-4-biphenyl | piperidin-1-yl |
| 230 | 3'-trifluoromethyl-4-biphenyl | piperazin-1-yl |
| 231 | 3'-trifluoromethyl-4-biphenyl | morpholin-4-yl |
| 232 | 3'-trifluoromethyl-4-biphenyl | azepan-1-yl |
| 233 | 3'-cyano-4-biphenyl | aziridin-1-yl |
| 234 | 3'-cyano-4-biphenyl | pyrrolidin-1-yl |
| 235 | 3'-cyano-4-biphenyl | piperidin-1-yl |
| 236 | 3'-cyano-4-biphenyl | piperazin-1-yl |
| 237 | 3'-cyano-4-biphenyl | morpholin-4-yl |
| 238 | 3'-cyano-4-biphenyl | azepan-1-yl |
| 239 | 3'-nitro-4-biphenyl | aziridin-1-yl |
| 240 | 3'-nitro-4-biphenyl | pyrrolidin-1-yl |
| 241 | 3'-nitro-4-biphenyl | piperidin-1-yl |
| 242 | 3'-nitro-4-biphenyl | piperazin-1-yl |
| 243 | 3'-nitro-4-biphenyl | morpholin-4-yl |
| 244 | 3'-nitro-4-biphenyl | azepan-1-yl |
| 245 | 3'-methoxy-4-biphenyl | aziridin-1-yl |
| 246 | 3'-methoxy-4-biphenyl | pyrrolidin-1-yl |
| 247 | 3'-methoxy-4-biphenyl | piperidin-1-yl |
| 248 | 3'-methoxy-4-biphenyl | piperazin-1-yl |
| 249 | 3'-methoxy-4-biphenyl | morpholin-4-yl |
| 250 | 3'-methoxy-4-biphenyl | azepan-1-yl |
| 251 | 4'-fluoro-4-biphenyl | aziridin-1-yl |
| 252 | 4'-fluoro-4-biphenyl | pyrrolidin-1-yl |

TABLE IV-continued

| No. | R³ | R⁴ |
|---|---|---|
| 253 | 4'-fluoro-4-biphenyl | piperidin-1-yl |
| 254 | 4'-fluoro-4-biphenyl | piperazin-1-yl |
| 255 | 4'-fluoro-4-biphenyl | morpholin-4-yl |
| 256 | 4'-fluoro-4-biphenyl | azepan-1-yl |
| 257 | 4'-chloro-4-biphenyl | aziridin-1-yl |
| 258 | 4'-chloro-4-biphenyl | pyrrolidin-1-yl |
| 259 | 4'-chloro-4-biphenyl | piperidin-1-yl |
| 260 | 4'-chloro-4-biphenyl | piperazin-1-yl |
| 261 | 4'-chloro-4-biphenyl | morpholin-4-yl |
| 262 | 4'-chloro-4-biphenyl | azepan-1-yl |
| 263 | 4'-trifluoromethyl-4-biphenyl | aziridin-1-yl |
| 264 | 4'-trifluoromethyl-4-biphenyl | pyrrolidin-1-yl |
| 265 | 4'-trifluoromethyl-4-biphenyl | piperidin-1-yl |
| 266 | 4'-trifluoromethyl-4-biphenyl | piperazin-1-yl |
| 267 | 4'-trifluoromethyl-4-biphenyl | morpholin-4-yl |
| 268 | 4'-trifluoromethyl-4-biphenyl | azepan-1-yl |
| 269 | 4'-cyano-4-biphenyl | aziridin-1-yl |
| 270 | 4'-cyano-4-biphenyl | pyrrolidin-1-yl |
| 271 | 4'-cyano-4-biphenyl | piperidin-1-yl |
| 272 | 4'-cyano-4-biphenyl | piperazin-1-yl |
| 273 | 4'-cyano-4-biphenyl | morpholin-4-yl |
| 274 | 4'-cyano-4-biphenyl | azepan-1-yl |
| 275 | 4'-nitro-4-biphenyl | aziridin-1-yl |
| 276 | 4'-nitro-4-biphenyl | pyrrolidin-1-yl |
| 277 | 4'-nitro-4-biphenyl | piperidin-1-yl |
| 278 | 4'-nitro-4-biphenyl | piperazin-1-yl |
| 279 | 4'-nitro-4-biphenyl | morpholin-4-yl |
| 280 | 4'-cyano-4-biphenyl | azepan-1-yl |
| 281 | 4'-methoxy-4-biphenyl | aziridin-1-yl |
| 282 | 4'-methoxy-4-biphenyl | pyrrolidin-1-yl |
| 283 | 4'-methoxy-4-biphenyl | piperidin-1-yl |
| 284 | 4'-methoxy-4-biphenyl | piperazin-1-yl |
| 285 | 4'-methoxy-4-biphenyl | morpholin-4-yl |
| 286 | 4'-methoxy-4-biphenyl | azepan-1-yl |

The compounds which comprise the first and second aspect of Category II wherein $R^2$ is equal to methyl, said compounds can be prepared by the procedure described herein below and outline in Scheme II. However, the artisan can substitute other procedures which facilitate the achievement of higher yields, purity, or which utilize readily available starting materials which can be introduced into the procedures outlined herein below. As is relates to the variations in $R^4$ for the first aspect of Category II compounds, in step (d) Scheme I above intermediate 4 is prepared. Other aspects or iterations of this aspect of Category II can be achieved by the artisan substituting $NH_3$, $NH_2CH_3$, $NH(CH_2CH_3)_2$, $NH(CH_3)(CH_2CH_3)$, $NH_2(CH_2CH_3)$, $NH_2[CH(CH_3)_2]$, and $NH[CH(CH_3)_2]_2$, as well as other $NHR^6R^7$ amines wherein $R^6$ and $R^7$ are each independently $C_1$-$C_8$ substituted or unsubstituted linear or branched hydrocarbyl units, for $NH(CH_3)_2$ in step (d). However, the conditions may be necessarily adjusted by the formulator using practices standard and known to the skilled artisan.

As it relates to compounds encompassed by the second aspect of Category II, wherein $R^6$ and $R^7$ can be taken together to form a heterocyclic ring having from 3 to 8 atoms, aziridine, pyrrolidine, piperidine, piperazine, 1H-azepine, and morpholine, for example, can be substituted for $NH(CH_3)_2$ in step (d) of Scheme I herein above. However, the conditions may be necessarily adjusted by the formulator using practices standard and known to the skilled artisan.

Likewise, 4'-trifluoromethyl-biphenyl-4-carbonyl chloride is replaced with 4'-fluoro-biphenyl-4-carbonyl chloride, 4'-chloro-biphenyl-4-carbonyl chloride, and the like to affect the full range of R units under Category II, first and second aspects.

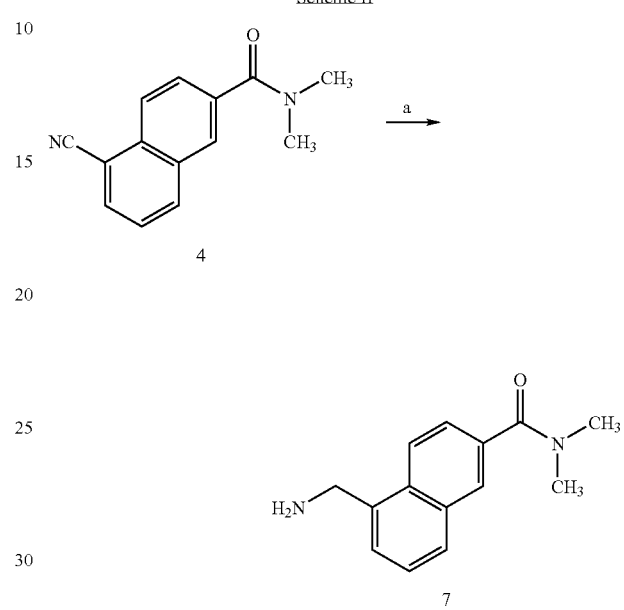

Reagents and conditions: (a) $H_2$/Raney $N_i$, $NH_4OH$, EtOH; rt, 4 days.

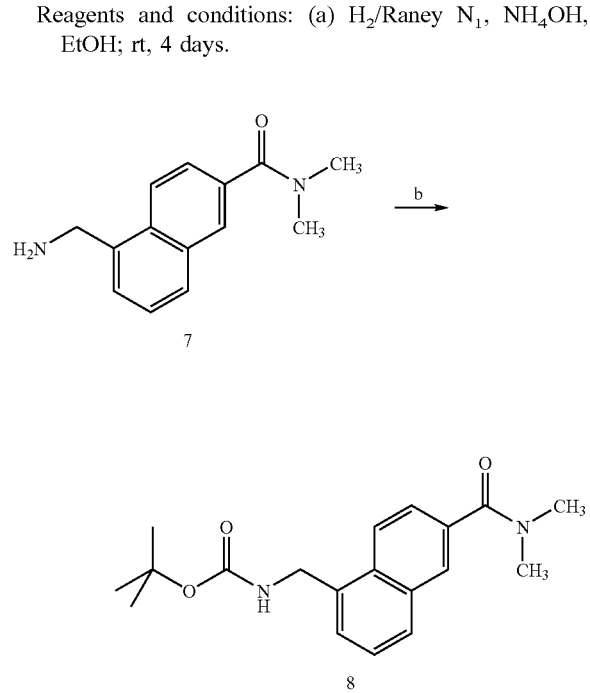

Reagents and conditions: (b) $(Boc)_2O$, $CH_2Cl_2$; rt, 2 hrs.

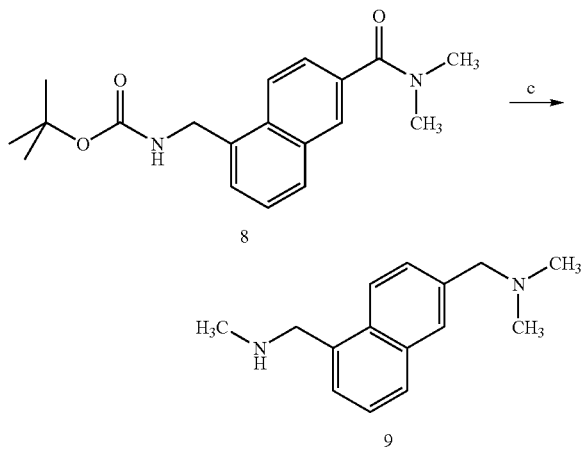

Reagents and conditions: (c) LAH, THF; 0° C. to reflux, 3 hr.

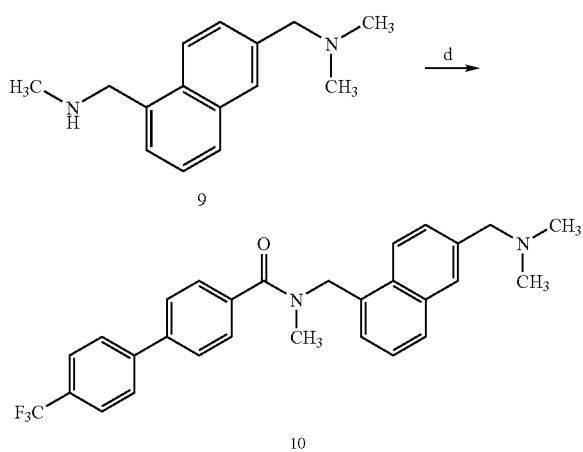

Reagents and conditions: (f) 4-(4'-CF$_3$—Ph)—Ph—COCl, CH$_2$Cl$_2$; rt, 2 hr.

EXAMPLE 2

4'-Trifluormethyl-biphenyl-4-carboxylic acid (6-dimethylaminomethyl-naphthalen-1-ylmethyl)-methyl-amide (10)

Preparation of 5-aminomethyl-naphthalene-2-carboxylic acid dimethylamide (7): A suspension of 5-cyano-naphthalene-2-carboxylic acid dimethylamide, 4, (18.93 g, 84.51 mmol), 28% NH$_4$OH (24 mL) and EtOH (500 mL) is reacted with hydrogen (1 atmosphere) in the presence of Ra—Ni (8 g) catalyst for 4 days. The catalyst is removed by filtration and the filtrate is concentrated in vacuo to afford 18.66 g (97% yield) of the desired product. $^1$H NMR (300 MHz, CD$_3$OD): δ 8.23 (d, J=8.7 Hz, 1H), 8.70-8.11 (m, 2H), 7.63-7.78 (m, 3H), 4.69 (s, 2H), 3.20, (s, 3H), 3.09 (s, 3H). LRMS: 228.99 (M+1), 211.96 (M+1-NH$_3$).

Preparation of (6-dimethylcarbamoyl-naphthalen-1-ylmethyl)-carbamic acid tert-butyl ester (8): To a room temperature solution of 5-aminomethyl-naphthalene-2-carboxylic acid dimethylamide, 7, (18.66 g, 81.84 mmol) and di-tert-butyldicarbonate (17.84 g, 81.84 mmol) in CH$_2$Cl$_2$ (200 mL) is stirred at room temperature for 1 hour. The solution is concentrated in vacuo and the residue purified over silica (EtOAc/hexane 1:4 to 1:1) to afford 20.46 g (76% yields) of the desired product as a light yellow solid. $^1$H NMR (300 MHz, CDCl$_3$): δ 8.04 (d, J=8.4 Hz, 1H), 7.92 (s, 1H), 7.85 (d, J=7.2 Hz, 1H), 7.42-7.58 (m, 3H), 4.91 (br, 1H), 4.78 (s, 2H), 4.78 (s, 2H), 3.11 (s, 6H), 1.48 (s, 9H). $^{13}$C NMR (75 MHz, CDCl$_3$): δ 171.7, 156.8, 134.3, 133.9, 133.4, 131.7, 129.8, 127.8, 127.2, 126.5, 125.2, 124.0, 61.3, 43.1, 39.9, 35.7, 14.9. LRMS: 323.17 (M+Na), 301.17 (M+1).

Preparation of (6-dimethylaminomethyl-naphthalen-1-ylmethyl)-methyl-amine (9): To a room temperature solution of (6-dimethylcarbamoyl-naphthalen-1-ylmethyl)-carbamic acid tert-butyl ester, 8, (20.45 g, 62.4 mmol) in anhydrous THF (300 mL) is added 1 M LAH in THF (125 mL, 2 eq.). After the addition is complete the resulting solution is heated at reflux for 3 hours. The reaction solution is then cooled in an ice bath and quenched by the addition of water (2.7 mL). The resulting mixture is dried over MgSO$_4$. The solid is removed by filtration and the filtrate concentrated in vacuo to afford 14.25 g of the desired product as a colorless oil. LRMS: 229.05 (M+1).

Preparation of 4'-trifluoromethyl-biphenyl-4-carboxylic acid (6-dimethylamino-methyl-naphthalen-1-ylmethyl)-methyl-amide HCl (10): A solution of (6-dimethylamino-methyl-naphthalen-1-ylmethyl)-methyl-amine, 9, (14.25 g, 62.50 mmol), and 4'-trifluoromethyl-biphenyl-4-carbonyl chloride (17.81 g, 62.50 mmol) in CH$_2$Cl$_2$ (500 mL) is stirred at room temperature for 1 hr. The white solid which forms is collected by filtration and rinsed twice with CH$_2$Cl$_2$ (100 mL) to afford 22.0 g (69% yield) of the desired product as a white solid. $^1$H NMR (300 MHz, CD$_3$OD): δ 8.37 (d, J=8.4 Hz, 1H), 8.15-7.56 (m, 13H), 5.31 (s, 2H), 5.31 and 5.14 (2×s, 2H, two rotamers), 3.17 and 2.93 (2×s, 9H, two rotamers). $^{13}$C NMR (75 MHz, CDCl$_3$): δ 172.0, 165.5, 143.9, 141.4, 135.8, 134.1, 132.4, 132.1, 130.0, 129.0, 128.7, 127.7, 127.6, 127.4, 126.7, 126.6, 125.2, 123.9, 117.1, 61.1, 53.3, 42.1, 36.6. 19F NMR (282 MHz, CD$_3$OD): δ 99.1. Mass Spec.: Calcd.: 477.5106; found HRMS: 477.5113; Formula: C$_{29}$H$_{27}$F$_3$N$_2$O+H, found LRMS: 477.27 (M+1).

The following are non-limiting examples of further compounds according to Category II of the present invention.

4'-Fluoro-biphenyl-4-carboxylic acid (6-diethylaminomethyl-naphthalen-1-ylmethyl)-methyl-amide: $^1$H NMR (300 MHz, CD$_3$OD): δ 7.03-8.38 (m, 14H), 5.27 (s, 2H), 4.56 (s, 2H), 3.10-3.40 (br, s, 4H), 2.90 (s, 3H), 1.41 (br, s, 6H); $^{13}$C NMR (75 MHz, CD$_3$OD): δ 173.2, 164.1 (d, J=240 0 Hz) 143.0, 137.4, 135.8, 135.2, 133.2, 130.0 (d, J=8 Hz), 129.9, 129.3, 129.1, 128.6, 128.0, 127.7, 126.6, 126.0, 124.9, 116.9, 116.6 (d, J=22 Hz), 57.1, 49.0, 37.7, 34.6, 9.1; $^{19}$F NMR (282 MHz, CD$_3$OD): δ 46.2. Mass Spec.: LRMS: 455.29 (M+H); Mass Spec.: LRMS: 455.29; HRMS: calcd.: 455.5863; for C$_{30}$H$_{31}$FN$_2$O, found: 455.5845.

3'-Trifluoromethyl-biphenyl-4-carboxylic acid (6-diethylaminomethyl-naphthalen-1-ylmethyl)-methyl-amide: $^1$H NMR (300 MHz, CD$_3$OD): δ 8.39 (d, J=8.4 Hz, 1H), 8.12-8.27 (m, 2H), 7.55-8.03 (m, 11H), 5.31 (s, 2H), 4.57 (s, 2H), 3.10-3.40 (br, s, 4H), 2.93 (s, 3H), 1.41 (br, s, 6H); $^{13}$C NMR (75 MHz, CD$_3$OD): δ 173.1, 142.3, 136.8, 135.9, 135.3, 134.4, 133.6, 133.2, 131.8, 131.3, 131.0, 129.6, 129.0, 128.9, 128.6, 128.4, 127.7, 126.2, 125.6, 124.6, 66.9, 57.2, 55.0, 37.6, 9.1; $^{19}$F NMR (282 MHz, CD$_3$OD): δ 98.8; Mass Spec.: LRMS: 505.29; HRMS: calcd.: 505.5935; for C$_{31}$H$_{31}$F$_3$N$_2$O+H, found: 505.5935.

Biphenyl-4-carboxylic acid (6-diethylaminomethyl-naphthalen-1-ylmethyl)-methyl-amide: $^1$H NMR (300 MHz, CDCl$_3$), δ 8.03 (br, s, 1H), 7.82 (m, 1H), 7.69-7.59 (m, 3H), 7.48-7.45 (m, 3H), 7.42-7.33 (m, 7H), 4.67 (s, 2H), 3.59 (s, 2H), 2.78 (s, 3H), 2.38 (d, J=7.5 Hz, 4H), 0.93 (t, J=7.5 Hz, 6H); $^{13}$C NMR (75 MHz, CDCl$_3$) δ 164.29, 142.41, 135.98, 134.99, 134.62, 134.21, 133.74, 133.43, 132.96, 132.71, 129.4, 129.2, 128.91, 128.87, 128.17, 127.53, 127.41, 126.94, 101.07, 56.97, 48.90, 37.65, 34.59, 9.08; LRMS: 437.17 (M+H).

4-Chloro-N-(6-diethylaminomethyl-naphthalen-1-ylmethyl)-N-methyl-benzamide: $^1$H NMR (300 MHz, CDCl$_3$) δ 8.23 (br, s, 1H), 8.18-7.84 (m, 3H), 7.68-7.42 (m, 4H), 7.24 (m, 2H), 4.65 (s, 2H), 3.59 (s, 2H), 3.54 (s, 3H), 2.43 (d, J=7.5 Hz, 4H), 0.87 (t, J=7.5 Hz, 6H); LRMS: 394.93 (M+H).

N-(6-Diethylaminomethyl-naphthalen-1-ylmethyl)-4-fluoro-N-methyl-benzamide: $^1$H NMR (300 MHz, CDCl$_3$) δ 8.22 (s, 1H), 8.20-7.87 (m, 3H), 7.66-7.41 (m, 4H), 7.23 (m, 2H), 4.69 (s, 2H), 3.59 (s, 2H), 3.57 (s, 3H), 2.44 (d, J=7.5 Hz, 4H), 0.88 (t, J=7.5 Hz, 6H); LRMS: 379.34 (M+H).

N-(6-Diethylaminomethyl-naphthalen-1-ylmethyl)-2-methoxy-N-methyl-benzamide: $^1$H NMR (300 MHz, CDCl$_3$) δ 8.41 (d, J=6.7 Hz, 1H), 8.34 (m, 1H), 7.89 (m, 1H), 7.86 (m, 1H), 7.84 (m, 1H), 7.52 (m, 4H), 7.34 (t, J=9.6 Hz, 1H), 4.65 (s, 2H), 3.59 (s, 2H), 3.56 (s, 3H), 281 (s, 3H), 2.41 (d, J=7.4 Hz, 4H), 0.89 (t, J=7.5 Hz, 6H); LRMS: 391.23 (M+H).

N-(6-Diethylaminomethyl-naphthalen-1-ylmethyl)-N-methyl-4-nitro-benzamide: $^1$H NMR (300 MHz, CDCl$_3$) δ 8.22 (s, 1H), 8.20-7.87 (m, 3H), 7.66-7.41 (m, 4H), 7.23 (m, 2H), 4.67 (s, 2H), 3.61 (s, 2H), 3.56 (s, 3H), 2.44 (d, J=7.5 Hz, 4H), 0.88 (t, J=7.5 Hz, 6H); LRMS: 406.21 (M+H).

N-(6-Diethylaminomethyl-naphthalen-1-ylmethyl)-4-fluoro-N-methyl-3-trifluoromethyl-benzamide: $^1$H NMR (300 MHz, CDCl$_3$) δ 8.18 (d, J=7.6 Hz, 1H), 8.15 (d, J=8.4 Hz, 11H), 7.86 (d, J=8.2 Hz, 1H), 7.12 (t, J=8.4 Hz, 1H), 7.58 (s, 1H), 7.54 (s, 11H), 7.47 (d, J=8.4 Hz, 11H), 7.45 (d, J=8.4 Hz, 1H), 7.14 (d, J=8.2 Hz, 1H), 4.66 (s, 2H), 3.60 (s, 2H), 3.56 (s, 3H), 2.42 (d, J=7.5 Hz, 4H), 0.89 (t, J=7.5 Hz, 6H); LRMS: 447.23 (M+H).

4'-Fluoro-biphenyl-4-carboxylic acid (6-piperidin-1-ylmethyl-naphthalen-1-ylmethyl)-methyl-amide: $^1$H NMR (300 MHz, CDCl$_3$) δ 8.30-8.08 (m, 3H), 7.89 (m, 1H), 7.64-7.54 (m, 8H), 7.32-7.16 (m, 2H), 5.08 (br, s, 2H), 3.64 (s, 2H), 2.92 (s, 3H), 2.51 (br, s, 4H), 1.91 (br, s, 4H), 1.41 (m, 2H); $^{13}$C NMR (75 MHz, CDCl$_3$) δ 164.4, 161.45 (d, J=240 Hz), 142.3, 136.1, 134.9, 134.6, 134.1, 133.7, 133.4, 133.2, 132.6, 130.3 (d, J=8 Hz), 129.0, 127.9, 127.3, 126.8, 125.7, 124.9, 116.0 (d, J=22 Hz), 61.1, 53.3, 48.6, 30.1, 23.0, 22.2; LRMS: 467.63 (M+H).

Biphenyl-4-carboxylic acid methyl-(6-piperidin-1-ylmethyl-naphthalen-1-ylmethyl)-amide: $^1$H NMR (300 MHz, CDCl$_3$) δ 8.38 (d, J=8.2 Hz, 1H), 8.17 (s, 1H), 7.83-7.47 (m, 5H), 7.31-7.19 (m, 6H), 7.19 (m, 2H), 4.66 (s, 2H), 3.60 (s, 2H), 2.77 (s, 3H), 2.52 (br, s, 4H), 1.53 (br, s, 6H); $^{13}$C NMR (75 MHz, CDCl$_3$) δ 164.4, 146.4, 142.4, 136.1, 134.9, 134.6, 134.2, 133.7, 133.5, 133.1, 132.7, 130.5, 129.2, 128.8, 128.1, 127.5, 127.4, 126.9, 100.2, 61.2, 53.3, 47.5, 30.0, 23.0, 22.2; LRMS: 449.34 (M+H) 471.63 (M+Na).

2-(4'-Fluoro-biphenyl-4-yl)-N-methyl-N-(6-pyrrolidin-1-ylmethyl-naphthalen-1-ylmethyl)-acetamide: $^1$H NMR (300 MHz, CDCl$_3$) δ 8.33 (d, J=8.2 Hz, 1H), 8.16 (s, 1H), 7.82-7.47 (m, 4H), 7.31-7.14 (m, 8H), 4.67 (s, 2H), 3.57 (s, 2H), 3.26 (s, 2H), 2.77 (s, 3H), 2.53 (br, s, 4H), 1.51 (br, s, 4H); $^{13}$C NMR (75 MHz, CDCl$_3$) δ 163.7, 161.0 (d, J=240 Hz), 141.6, 136.2, 135.1, 134.6, 134.2, 133.7, 133.5, 133.2, 132.6, 129.3 (d, J=8 Hz), 129.0, 127.9, 127.3, 126.8, 125.7, 124.9, 116.1 (d, J=22 Hz), 68.6, 58.7, 53.6, 47.2, 32.6, 23.2; LRMS: 457.23 (M+H).

4-Chloro-N-methyl-N-(6-pyrrolidin-1-ylmethyl-naphthalen-1-ylmethyl)-benzamide: $^1$H NMR (300 MHz, CDCl$_3$) δ 8.29-8.24 (m, 2H), 8.17 (br, s, 1H), 8.14 (br, s, 1H), 7.67-7.59 (m, 4H), 7.55-7.47 (m, 2H), 4.77 (s, 2H), 3.65 (s, 2H), 2.77 (s, 3H), 2.53 (br, s, 4H), 1.51 (br, s, 4H); $^{13}$C NMR (75 MHz, CDCl$_3$) δ 164.7, 158.3, 136.6, 135.2, 133.7, 128.8, 126.9, 126.6, 122.2, 117.5, 115.0, 114.7, 112.6, 111.7, 110.9, 56.7, 54.0, 49.3, 31.5, 23.0; LRMS: 394.2 (M+H).

2-Methoxy-N-methyl-N-(6-pyrrolidin-1-ylmethyl-naphthalen-1-ylmethyl)-benzamide: $^1$H NMR (300 MHz, CDCl$_3$) δ 8.22 (d, J=6.0 Hz, 1H), 7.89-7.80 (m, 2H), 7.64 (t, J=6.8 Hz, 1H), 7.58-7.45 (m, 3H), 7.29-7.08 (m, 3H), 4.78 (s, 2H), 3.93 (s, 3H), 3.68 (s, 2H), 2.76 (s, 3H), 2.55 (m, 4H), 1.53 (m, 4H); $^{13}$C NMR (75 MHz, CDCl$_3$) δ 165.8, 158.1, 136.9, 135.2, 133.8, 128.8, 128.4, 128.0, 126.9, 126.7, 122.2, 117.5, 115.0, 114.7, 112.6, 111.7, 111.0, 56.7, 53.8, 51.3, 35.1, 31.5, 23.0; LRMS: 389.2 (M+H).

4'-Trifluoromethyl-biphenyl-4-carboxylic acid methyl-(6-piperidin-1-ylmethyl-naphthalen-1-ylmethyl)-amide: $^1$H NMR (300 MHz, CD$_3$OD): δ 8.32 (d, J=8.2 Hz, 1H), 8.18 (m, 2H), 7.96 (m, 3H), 7.73-7.60 (m, 8H), 5.2 (s, 2H), 4.49 (s, 2H), 3.48 (m, 2H), 3.06 (m, 2H), 2.89 (s, 3H), 1.83 (m, 6H). $^{13}$C NMR (75 MHz, CD$_3$OD) δ 173.47, 145.39, 142.79, 137.43, 135.62, 134.14, 133.99, 133.70, 131.42, 131.00, 130.57, 130.67, 129.32, 129.17, 128.98, 128.57, 128.16, 127.93, 127.34, 126.36, 62.18, 54.67, 38.30, 35.10, 24.56, 23.23. LRMS: 517.35 (M+1).

3'-Trifluoromethyl-biphenyl-4-carboxylic acid methyl-(6-piperidin-1-ylmethyl-naphthalen-1-ylmethyl)-amide: $^1$H NMR (300 MHz, CD$_3$OD): δ 8.31 (s, 1H), 8.12 (s, 1H), 8.00-7.79 (m, 5H), 7.79-7.59 (m, 7H), 5.25 (s, 2H), 4.46 (s, 2H), 3.47 (m, 2H), 3.01 (m, 2H), 2.88 (s, 3H), 2.01-1.68 (m, 6H). $^{13}$C NMR (75 MHz, CD$_3$OD) δ 173.5, 142.8, 142.6, 137.3, 135.6, 134.0, 133.7, 132.9, 132.5, 132.2, 131.4, 130.5, 130.2, 129.8, 129.2, 128.8, 128.5, 128.1, 127.8, 126.3, 126.0, 125.0, 62.0, 54.5, 38.1, 34.9, 24.5, 23.1. LRMS: 517.35 (M+1).

4'-Trifluoromethyl-biphenyl-4-carboxylic acid (6-diethylaminomethyl-naphthalen-1-ylmethyl)-methyl-amide: $^1$H NMR (300 MHz, CD$_3$OD): δ 8.27 (d, J=8.5 Hz, 1H), 8.02 (m, 2H), 7.91-7.80 (m, 3H), 7.76-7.60 (m, 6H), 7.46 (m, 2H), 5.2 (s, 2H), 4.45 (s, 2H), 3.28 (m, 4H), 2.81 (s, 3H), 1.31 (m, 6H). $^{13}$C NMR (75 MHz, CD$_3$OD) δ 170.0, 163.4, 144.3, 142.6, 136.0, 135.5, 133.4, 132.4, 131.5, 129.9, 129.8, 129.3, 128.9, 128.7, 128.6, 128.2, 126.3, 125.0, 120.5, 116.6, 63.8, 57.6, 56.0, 42.9, 9.6. LRMS: 503.34 (M+1).

3'-Trifluoromethyl-biphenyl-4-carboxylic acid (6-diethylaminomethyl-naphthalen-1-ylmethyl)-methyl-amide: $^1$H NMR (300 MHz, CD$_3$OD): δ 8.24 (d, J=8.7 Hz, 1H), 8.04 (m, 2H), 7.93-7.81 (m, 3H), 7.77-7.59 (m, 6H), 7.43 (m, 2H), 5.20 (s, 2H), 4.45 (s, 2H), 3.27 (m, 4H), 2.80 (s, 3H), 1.29 (m, 6H). $^{13}$C NMR (75 MHz, CD$_3$OD) δ. 170.3, 143.2, 142.5, 136.2, 135.6, 135.2, 133.4, 132.8, 132.2, 131.3, 130.1, 129.7, 129.5, 128.8, 128.6, 128.2, 126.6, 126.2, 125.9, 125.0, 120.7, 116.7, 64.3, 57.7, 55.9, 42.8, 9.7; LRMS: 503.38 (M+1).

2-Cyano-N-methyl-3-phenyl-N-(6-pyrrolidin-1-ylmethyl-naphthalen-1-ylmethyl)-acrylamide: $^1$H NMR (300 MHz, CDCl$_3$) δ 8.11 (br, s, 1H), 7.92 (d, J=6.0 Hz, 1H), 7.85-7.80 (m, 3H), 7.70-7.38 (m, 6H), 5.17 (s, 1H), 4.79 (s, 2H), 3.63 (s, 2H), 2.81 (s, 3H), 2.49 (br, s, 4H), 1.51 (br, s, 4H); $^{13}$C NMR (75 MHz, CDCl$_3$) δ 165.6, 155.9, 152.6, 133.7, 132.7, 132.1, 132.3, 131.9, 131.8, 131.4, 130.4, 129.6, 129.4, 128.1, 126.8, 116.5, 112.8, 102.5, 58.7, 53.6, 47.3, 32.7, 23.3; LRMS: 410.28 (M+H).

Other compounds which comprise the first aspect of Category II that are not specifically exemplified herein include the following:

4'-Fluoro-biphenyl-4-carboxylic acid (6-amino-methyl-naphthalen-1-ylmethyl)-methyl-amide;
4'-Chloro-biphenyl-4-carboxylic acid (6-amino-methyl-naphthalen-1-ylmethyl)-methyl-amide;
4'-Cyano-biphenyl-4-carboxylic acid (6-amino-methyl-naphthalen-1-ylmethyl)-methyl-amide;
4'-Nitro-biphenyl-4-carboxylic acid (6-amino-methyl-naphthalen-1-ylmethyl)-methyl-amide;
4'-Trifluoromethyl-biphenyl-4-carboxylic acid (6-amino-methyl-naphthalen-1-ylmethyl)-methyl-amide;
4'-Methyl-biphenyl-4-carboxylic acid (6-amino-methyl-naphthalen-1-ylmethyl)-methyl-amide;
4'-Methoxy-biphenyl-4-carboxylic acid (6-amino-methyl-naphthalen-1-ylmethyl)-methyl-amide;
4'-Fluoro-biphenyl-4-carboxylic acid (6-dimethylamino-methyl-naphthalen-1-ylmethyl)-methyl-amide;
4'-Chloro-biphenyl-4-carboxylic acid (6-dimethylamino-methyl-naphthalen-1-ylmethyl)-methyl-amide;
4'-Cyano-biphenyl-4-carboxylic acid (6-dimethylamino-methyl-naphthalen-1-ylmethyl)-methyl-amide;
4'-Nitro-biphenyl-4-carboxylic acid (6-dimethylamino-methyl-naphthalen-1-ylmethyl)-methyl-amide;
4'-Methyl-biphenyl-4-carboxylic acid (6-dimethylamino-methyl-naphthalen-1-ylmethyl)-methyl-amide;
4'-Methoxy-biphenyl-4-carboxylic acid (6-dimethylamino-methyl-naphthalen-1-ylmethyl)-methyl-amide;
4'-Cyano-biphenyl-4-carboxylic acid (6-diethylamino-methyl-naphthalen-1-ylmethyl)-methyl-amide;
4'-Methyl-biphenyl-4-carboxylic acid (6-diethylamino-methyl-naphthalen-1-ylmethyl)-methyl-amide;
4'-Methoxy-biphenyl-4-carboxylic acid (6-diethylamino-methyl-naphthalen-1-ylmethyl)-methyl-amide;
4'-Fluoro-biphenyl-4-carboxylic acid (6-methylamino-methyl-naphthalen-1-ylmethyl)-methyl-amide;
4'-Chloro-biphenyl-4-carboxylic acid (6-methylamino-methyl-naphthalen-1-ylmethyl)-methyl-amide;
4'-Cyano-biphenyl-4-carboxylic acid (6-methylamino-methyl-naphthalen-1-ylmethyl)-methyl-amide;
4'-Nitro-biphenyl-4-carboxylic acid (6-methylamino-methyl-naphthalen-1-ylmethyl)-methyl-amide;
4'-Trifluoromethyl-biphenyl-4-carboxylic acid (6-methylamino-methyl-naphthalen-1-ylmethyl)-methyl-amide;
4'-Methyl-biphenyl-4-carboxylic acid (6-methylamino-methyl-naphthalen-1-ylmethyl)-methyl-amide;
4'-Methoxy-biphenyl-4-carboxylic acid (6-methylamino-methyl-naphthalen-1-ylmethyl)-methyl-amide;
4'-Fluoro-biphenyl-4-carboxylic acid (6-ethylamino-methyl-naphthalen-1-ylmethyl)-methyl-amide;
4'-Chloro-biphenyl-4-carboxylic acid (6-ethylamino-methyl-naphthalen-1-ylmethyl)-methyl-amide;
4'-Cyano-biphenyl-4-carboxylic acid (6-ethylamino-methyl-naphthalen-1-ylmethyl)-methyl-amide;
4'-Nitro-biphenyl-4-carboxylic acid (6-ethylamino-methyl-naphthalen-1-ylmethyl)-methyl-amide;
4'-Trifluoromethyl-biphenyl-4-carboxylic acid (6-ethylamino-methyl-naphthalen-1-ylmethyl)-methyl-amide;
4'-Methyl-biphenyl-4-carboxylic acid (6-ethylamino-methyl-naphthalen-1-ylmethyl)-methyl-amide;
4'-Methoxy-biphenyl-4-carboxylic acid (6-ethylamino-methyl-naphthalen-1-ylmethyl)-methyl-amide;
4'-Fluoro-biphenyl-4-carboxylic acid (6-methylethylamino-methyl-naphthalen-1-ylmethyl)-methyl-amide;
4'-Chloro-biphenyl-4-carboxylic acid (6-methylethylamino-methyl-naphthalen-1-ylmethyl)-methyl-amide;
4'-Cyano-biphenyl-4-carboxylic acid (6-methylethylamino-methyl-naphthalen-1-ylmethyl)-methyl-amide;
4'-Nitro-biphenyl-4-carboxylic acid (6-methylethylamino-methyl-naphthalen-1-ylmethyl)-methyl-amide;
4'-Trifluoromethyl-biphenyl-4-carboxylic acid (6-methylethylamino-methyl-naphthalen-1-ylmethyl)-methyl-amide;
4'-Methyl-biphenyl-4-carboxylic acid (6-methylethylamino-methyl-naphthalen-1-ylmethyl)-methyl-amide; and
4'-Methoxy-biphenyl-4-carboxylic acid (6-methylethylamino-methyl-naphthalen-1-ylmethyl)-methyl-amide.

Further compounds according to Category I wherein $R^6$ and $R^7$ are taken together to form a ring comprising 3 to 8 atoms:

4'-Fluoro-biphenyl-4-carboxylic acid methyl-(6-pyrrolidin-1-ylmethyl-naphthalen-1-ylmethyl)-amide;
4'-Nitro-biphenyl-4-carboxylic acid methyl-(6-pyrrolidin-1-ylmethyl-naphthalen-1-ylmethyl)-amide;
4'-Cyano-biphenyl-4-carboxylic acid methyl-(6-pyrrolidin-1-ylmethyl-naphthalen-1-ylmethyl)-amide;
4'-Trifluoromethyl-biphenyl-4-carboxylic acid methyl-(6-pyrrolidin-1-ylmethyl-naphthalen-1-ylmethyl)-amide;
4'-Methyl-biphenyl-4-carboxylic acid methyl-(6-pyrrolidin-1-ylmethyl-naphthalen-1-ylmethyl)-amide;
4'-Methoxy-biphenyl-4-carboxylic acid methyl-(6-pyrrolidin-1-ylmethyl-naphthalen-1-ylmethyl)-amide;
4'-Fluoro-biphenyl-4-carboxylic acid methyl-(6-piperidin-1-ylmethyl-naphthalen-1-ylmethyl)-amide;
4'-Chloro-biphenyl-4-carboxylic acid methyl-(6-piperidin-1-ylmethyl-naphthalen-1-ylmethyl)-amide;
4'-Nitro-biphenyl-4-carboxylic acid methyl-(6-piperidin-1-ylmethyl-naphthalen-1-ylmethyl)-amide;
4'-Cyano-biphenyl-4-carboxylic acid methyl-(6-piperidin-1-ylmethyl-naphthalen-1-ylmethyl)-amide;
4'-Methyl-biphenyl-4-carboxylic acid methyl-(6-piperidin-1-ylmethyl-naphthalen-1-ylmethyl)-amide;
4'-Methoxy-biphenyl-4-carboxylic acid methyl-(6-piperidin-1-ylmethyl-naphthalen-1-ylmethyl)-amide;
4'-Fluoro-biphenyl-4-carboxylic acid methyl-(6-piperazin-1-ylmethyl-naphthalen-1-ylmethyl)-amide;
4'-Chloro-biphenyl-4-carboxylic acid methyl-(6-piperazin-1-ylmethyl-naphthalen-1-ylmethyl)-amide;
4'-Nitro-biphenyl-4-carboxylic acid methyl-(6-piperazin-1-ylmethyl-naphthalen-1-ylmethyl)-amide;
4'-Cyano-biphenyl-4-carboxylic acid methyl-(6-piperazin-1-ylmethyl-naphthalen-1-ylmethyl)-amide;
4'-Trifluoromethyl-biphenyl-4-carboxylic acid methyl-(6-piperazin-1-ylmethyl-naphthalen-1-ylmethyl)-amide;
4'-Methyl-biphenyl-4-carboxylic acid methyl-(6-piperazin-1-ylmethyl-naphthalen-1-ylmethyl)-amide;
4'-Methoxy-biphenyl-4-carboxylic acid methyl-(6-piperazin-1-ylmethyl-naphthalen-1-ylmethyl)-amide;
4'-Fluoro-biphenyl-4-carboxylic acid methyl-(6-aziridin-1-ylmethyl-naphthalen-1-ylmethyl)-amide;
4'-Chloro-biphenyl-4-carboxylic acid methyl-(6-aziridin-1-ylmethyl-naphthalen-1-ylmethyl)-amide;
4'-Nitro-biphenyl-4-carboxylic acid methyl-(6-aziridin-1-ylmethyl-naphthalen-1-ylmethyl)-amide;
4'-Cyano-biphenyl-4-carboxylic acid methyl-(6-aziridin-1-ylmethyl-naphthalen-1-ylmethyl)-amide;
4'-Trifluoromethyl-biphenyl-4-carboxylic acid methyl-(6-aziridin-1-ylmethyl-naphthalen-1-ylmethyl)-amide;
4'-Methyl-biphenyl-4-carboxylic acid methyl-(6-aziridin-1-ylmethyl-naphthalen-1-ylmethyl)-amide;

4'-Methoxy-biphenyl-4-carboxylic acid methyl-(6-aziridin-1-ylmethyl-naphthalen-1-ylmethyl)-amide;
4'-Fluoro-biphenyl-4-carboxylic acid methyl-(6-morpholin-4-ylmethyl-naphthalen-1-ylmethyl)-amide;
4'-Chloro-biphenyl-4-carboxylic acid methyl-(6-morpholin-4-ylmethyl-naphthalen-1-ylmethyl)-amide;
4'-Nitro-biphenyl-4-carboxylic acid methyl-(6-morpholin-4-ylmethyl-naphthalen-1-ylmethyl)-amide;
4'-Cyano-biphenyl-4-carboxylic acid methyl-(6-morpholin-4-ylmethyl-naphthalen-1-ylmethyl)-amide;
4'-Trifluoromethyl-biphenyl-4-carboxylic acid methyl-(6-morpholin-4-ylmethyl-naphthalen-1-ylmethyl)-amide;
4'-Methyl-biphenyl-4-carboxylic acid methyl-(6-morpholin-4-ylmethyl-naphthalen-1-ylmethyl)-amide;
4'-Methoxy-biphenyl-4-carboxylic acid methyl-(6-morpholin-4-ylmethyl-naphthalen-1-ylmethyl)-amide;
4'-Fluoro-biphenyl-4-carboxylic acid methyl-(6-azepan-1-ylmethyl-naphthalen-1-ylmethyl)-amide;
4'-Chloro-biphenyl-4-carboxylic acid methyl-(6-azepan-1-ylmethyl-naphthalen-1-ylmethyl)-amide;
4'-Nitro-biphenyl-4-carboxylic acid methyl-(6-azepan-1-ylmethyl-naphthalen-1-ylmethyl)-amide;
4'-Cyano-biphenyl-4-carboxylic acid methyl-(6-azepan-1-ylmethyl-naphthalen-1-ylmethyl)-amide;
4'-Trifluoromethyl-biphenyl-4-carboxylic acid methyl-(6-azepan-1-ylmethyl-naphthalen-1-ylmethyl)-amide;
4'-Methyl-biphenyl-4-carboxylic acid methyl-(6-azepan-1-ylmethyl-naphthalen-1-ylmethyl)-amide; and
4'-Methoxy-biphenyl-4-carboxylic acid methyl-(6-azepan-1-ylmethyl-naphthalen-1-ylmethyl)-amide.

However, other compounds according to Category II of the present invention can be prepared by the method of Scheme I or by modifications made to Scheme II which are well understood by the artisan of ordinary skill.

Compounds listed and described herein above have been found in many instances to exhibit activities ($IC_{50}$ in the cell based assay described herein below or ones which are referenced herein) at a level below 1 micromolar (µM).

Each of the disease states or conditions which the formulator desires to treat may require differing levels or amounts of the compounds described herein to obtain a therapeutic level. The formulator can determine this amount by any of the common testing procedures known to the artisan.

Formulations

The present invention also relates to compositions or formulations which comprise the melanin concentrating hormone (MCH) antagonists according to the present invention. In general, the compositions of the present invention comprise:
a) an effective amount of one or more melanin concentrating hormone antagonists according to the present; and
b) one or more acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the knowledge that selected compounds of the present invention have improved cellular potency, pharmacokinetic properties, as well as improved oral bioavailability.

Non-limiting examples of compositions according to the present invention include:
a) from about 0.1 mg to about 5000 mg of one or more melanin concentrating hormone antagonists according to the present invention; and
b) one or more excipient.

Another embodiment according to the present invention relates to the following composition:
a) from about 1 mg to about 1000 mg of one or more melanin concentrating hormone antagonists according to the present invention; and
b) one or more excipient.

A further embodiment according to the present invention relates to the following composition:
a) from about 10 mg to about 500 mg of one or more melanin concentrating hormone antagonists according to the present invention; and
b) one or more excipient.

A yet further embodiment according to the present invention relates to the following composition:
a) from about 100 mg to about 1000 mg of one or more melanin concentrating hormone antagonists according to the present invention; and
b) one or more excipient.

The term "effective amount" as used herein means "an amount of one or more melanin concentrating hormone antagonists, effective at dosages and for periods of time necessary to achieve the desired result." An effective amount may vary according to factors known in the art, such as the disease state, age, sex, and weight of the human or animal and affinity of drug for target receptor being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

Another aspect of the present invention relates to compositions which are anti-obesity compositions and therefore provide body weight control or maintenance of weight loss, the compositions of the present invention comprise:
a) an effective amount of one or more melanin concentrating hormone antagonists according to the present invention in an amount effective for providing body weight control or maintenance of weight loss;
b) one or more pharmaceutically acceptable excipients.

For the purposes of the present invention the term "body weight control or maintenance of weight loss" is defined herein as "the ability of a compound of the present invention to provide effective loss of body mass and to provide an effective maintenance of body mass at a particular body mass value (body weight)."

A second aspect of the present invention relates to compositions which are body weight gain controlling compositions and therefore provide weight gain control, the compositions of the present invention comprise:

a) an effective amount of one or more melanin concentrating hormone agonists according to the present invention in an amount effective for providing control of weight gain; and
b) one or more acceptable excipients.

A further aspect of the present invention relates to compositions which are anxiolytic and antidepressant compositions and therefore provide control of anxiety and/or relief from depression, the compositions of the present invention comprise:
a) an effective amount of one or more melanin concentrating hormone agonists according to the present invention in an amount effective for providing control of anxiety and/or relief from depression; and
b) one or more acceptable excipients.

The compositions of this invention are typically provided in unit dosage form. For the purposes of the present invention the term "unit dosage form" is defined herein as comprising an effective amount of one or more melanin concentrating hormone antagonists. The compositions of the present invention contain in one embodiment from about 0.1 mg to about 5000 mg of one or more melanin concentrating hormone antagonists, while in other embodiments the compositions comprise from about 10 mg to about 500 mg, or from about 100 mg to about 1000 mg respectively.

Non-limiting examples of substances which can serve as pharmaceutically-acceptable excipients or components thereof are sugars, inter alia, lactose, glucose and sucrose, sorbitol, mannitol; starches, inter alia, corn starch and potato starch; cellulose and its derivatives, inter alia, sodium carboxymethyl cellulose, ethyl cellulose, and methyl cellulose; powdered tragacanth; malt; gelatin; talc; solid lubricants, such as stearic acid and magnesium stearate; vegetable oils, propylene glycol, glycerin, and polyethylene glycol; agar; alginic acid; wetting agents and lubricants, inter alia, sodium lauryl sulfate; coloring agents; flavoring agents; tableting agents, stabilizers; antioxidants; preservatives; pyrogen-free water; isotonic saline; and buffers.

Standard pharmaceutical formulation techniques are disclosed in *Remington's Pharmaceutical Sciences*, Mack Publishing Company, Easton, Pa., latest edition and *Peptide and Protein Drug Delivery*, Marcel Dekker, NY, 1991. Dosage forms useful for making the compositions of the present invention or which are compatible with the methods of use as described herein below are described in the following references, all incorporated by reference herein: *Modern Pharmaceutics*, Chapters 9 and 10 (Banker & Rhodes, editors, 1979); Lieberman et al., *Pharmaceutical Dosage Forms. Tablets* (1981); and Ansel, *Introduction to Pharmaceutical Dosage Forms* 2d Edition (1976); *Standard-Release Injectable Products*, ed. J. Senior and M. Radomsk, Interpharm Press; Denver, Co. (2000).

Method of Use

Many human and mammalian disorders result from too much body mass (obesity or other over weight condition). Controlling body mass is a first step in preventing, as well as effectively treating many diseases and disease states. Among the disorders which are modulated, attenuated, abated, or otherwise controlled by the compounds of the present invention which serve as antagonists of MCH activity, is human obesity. This condition has been shown to be directly related to a wide range of disorders. The compounds of the present invention are capable of treating diseases by acting as antagonists of MCH activity with minimal, little, or no activity involving the $5$-$HT_{2c}$ receptor.

As antagonists of MCH action upon the MCH receptor, the compounds of the present invention are useful in treating disorders that are mediated by MCH through the MCH receptor. Additional disorders other than obesity and food intake related illnesses that are mediated by MCH through the MCH receptor are thyroid hormone secretion, diuresis and water/electrolyte homeostasis, memory, sleep and arousal, anxiety and depression, seizure and in treatment of neurodegeneration or psychiatric disorders.

The compounds of the present invention have improved cellular potency and pharmacokinetic properties and this advantage is made use of by the fact the third aspect of the present invention as a whole, relates to a method for controlling obesity, and the subsequent weight management after weight loss. This is achieved by administering to a human or a higher mammal an effective amount of one or more of the compounds (analogs) as described herein.

Melanin Concentrating Hormone (MCH) activity, to which the antagonists of the present invention are directed, and as discussed herein above, is not limited to modulation of food intake as effects on the hypothalamic-pituitary axis have been reported.[2]

Further, as antagonists, it has been reported by Chaki et al.[3] that antagonists of melanin concentrating hormone have shown significantly reduced immobility time in the forced swimming test in rats, indicating antidepressant-like effects. In addition this group has reported significantly reversed swim stress-induced anxiety in the elevated plus-maze test in rats and stress-induced hyperthermia in mice. These finding indicate that MCH antagonists have demonstrated anxiolytic and antidepressant activity.

Utilizing the melanin concentrating hormone (MCH) antagonists of the present invention will therefore affect a variety of diseases, disease states, conditions, or syndromes resulting from body weight disorders, inter alia, insulin resistance, glucose intolerance, Type-2 diabetes mellitus, coronary artery disease, elevated blood pressure, hypertension, dyslipidaemia, cancer (e.g., endometrial, cervical, ovarian, breast, prostate, gallbladder, colon), menstrual irregularities, hirsutism, infertility, gallbladder disease, restrictive lung disease, sleep apnea, gout, osteoarthritis, and thromboembolic disease.

2. Critical Rev. *in Neurobiol.*, Nahon, 8, 221-262 (1994).
3. J. Pharmacol. Exp. Ther. 2005 May; 313(2):831-9.

Although the melanin concentrating hormone antagonists of the present invention are discrete chemical entities, the method of delivery or the method of use may be coupled with other suitable drug delivery systems. For example, a drug delivery technique useful for the compounds of the present invention is the conjugation of the compound to an active molecule capable of being transported through a biological barrier.[4] A specific example constitutes the coupling of the compound of the invention to fragments of insulin to achieve transport across the blood brain barrier.[5]

4. Zlokovic, B. V., *Pharmaceutical Research*, Vol. 12, pp. 1395-1406 (1995).
5. Fukuta, M., et al. *Pharmaceutical Res., Vol.* 11, pp. 1681-1688 (1994).

For general reviews of technologies for drug delivery suitable for the compounds of the invention see:

The compounds of the present invention which are selective antagonists at the MCH-R1 receptor over the $5$-$HT_{2c}$ receptor are suitable for use the following:

A method for controlling the body weight of humans and higher mammals, said method comprising administering to a human or higher mammal an effective amount of one or more selective antagonist of the present invention, including all enantiomeric and diasteriomeric forms and salts thereof.

A method for controlling weight gain in humans and higher mammals, said method comprising administering to a human or higher mammal an effective amount of one or more selective antagonist of the present invention, including all enantiomeric and diasteriomeric forms and salts thereof.

A method for controlling anxiety in humans and higher mammals, said method comprising administering to a human or higher mammal an effective amount of one or more selective antagonist of the present invention, including all enantiomeric and diasteriomeric forms and salts thereof.

A method for controlling depression in humans and higher mammals, said method comprising administering to a human or higher mammal an effective amount of one or more selective antagonist of the present invention, including all enantiomeric and diasteriomeric forms and salts thereof.

A method for controlling in humans one or more diseases, disease states, conditions, or syndromes relating to behavior, said diseases, disease states, conditions, or syndromes are chosen from anxiety and depression, memory impairment (including learning), muscle atrophy, and nerve growth and repair comprising administering an effective amount of one or more selective antagonist of the present invention, including all enantiomeric and diasteriomeric forms and salts thereof.

A method for controlling in humans one or more diseases, disease states, conditions, or syndromes resulting from body weight disorders, said diseases, disease states, conditions, or syndromes are chosen from insulin resistance, glucose intolerance, Type-2 diabetes mellitus, coronary artery disease, elevated blood pressure, hypertension, dyslipidaemia, menstrual irregularities, hirsutism, gallbladder disease, restrictive lung disease, sleep apnea, gout, osteoarthritis, and thromboembolic disease, said method comprising administering to a human an effective amount of one or more selective antagonist of the present invention, including all enantiomeric and diasteriomeric forms and salts thereof.

Procedures

Binding and Functional Assays for Melanin Concentrating Hormone (MCH)

In vitro binding and function assays are performed on membranes derived from cells or tissues expressing endogenous MCH1R. Competition binding assays are performed to identify high affinity compounds. Briefly, either radiolabeled or europium labeled MCH with varying concentrations of competitor compound which are incubated with membranes expressing the receptor. Rat brain membrane or cell lines, including but not limited to human Kelly neuroblastoma cells, A-431 epidermoid cells, and rat PC-12 cells are known to express endogenous MCH1R and are used in the assay. Binding is allowed to proceed until equilibrium is reached then bound labeled MCH is separated from free MCH by capturing membranes onto a filter. The filters are washed to remove loosely associated MCH and labeled MCH is quantified. Data is analyzed and $IC_{50}$ and $K_i$ are calculated to determine compound affinity.

MCH function assays are performed in an analogous manner to the binding assay. Competition assays are performed with a single concentration of MCH and varying concentrations of compound. Function is assayed using GTP binding or a functional response (e.g. Calcium uptake, MAP/ERK activation) because the MCH1R is a G-protein coupled receptor that couples the $G_{i/o}$ and $G_q$ proteins and has been shown to elicit these cellular functional responses. The assay can be performed on the same membranes as used for the binding assays. There are readily available kits for measuring GTP binding to membranes (e.g. Perkin Elmer Life Sciences). Data is analyzed and $IC_{50}$ values are generated to determine whether the compound is an agonist or antagonist.

Binding assays for serotonin receptor, 5-$HT_{2c}$ receptor MCH antagonist compounds are evaluated for binding to the serotonin 5-$HT_{2c}$ receptor to determine receptor selectivity. Binding activity is assessed using a competitive assay with $^3$H-mesulergine (Perkin Elmer), a 5-$HT_{2c}$ selective ligand, on membrane containing the 5-$HT_{2c}$ receptor. Briefly, 1 nM $^3$H-mesulergine and varying concentrations of the compound are incubated with 5-$HT_{2c}$ receptor membranes, following an incubation period, the membranes are washed and $^3$H-mesulergine bound to membranes is measured in a liquid scintillation counter. The amount of bound $^3$H-mesulergine at the varying concentration of competitor compound is used to derive the affinity ($K_i$) of the compound for the 5-$HT_{2c}$ receptor. 5-$HT_{2c}$ receptor containing membranes are readily available from several companies including Perkin-Elmer and Euroscreen.

The following table shows $IC_{50}$ (nM) binding data for selected compounds at both the MCH1R and 5-$HT_{2c}$ receptors.

TABLE V

| Compound | MCH1R | 5-HT2C |
| --- | --- | --- |
| 4'-Fluoro-biphenyl-4-carboxylic acid (6-dimethyl-aminomethylnaphthalan-1-ylmethyl)-amide | 12 | 1125 |
| 4'-Trifluoromethyl-biphenyl-4-carboxylic acid (6-diethylaminomethyl-naphthalen-1-ylmethyl)-methyl-amide | 70 | 2058 |

Receptor Ligand Selectivity

The compounds of the present invention will interact preferentially (i.e., selectively) with MCH-1R relative to 5-$HT_{2c}$ receptors. Selectivity is particularly important when the compounds are administered to humans or other animals, to minimize the number of side effects associated with their administration. For example, MCH-1R selectivity of a compound relative to 5-$HT_{2c}$ is defined herein as the ratio of the $EC_{50}$ of the compound for an MCH-1R receptor ("MCH-1R-$EC_{50}$") over the $EC_{50}$ of the compound for the 5-$HT_{2c}$ (5-$HT_{2c}$-$EC_{50}$) receptor, the $EC_{50}$ values being measured as described above. The formulas are as follows:

MCH-1R/5-$HT_{2c}$ selectivity=[MCH-1R-$EC_{50}$]/[5-$HT_{2c}$-$EC_{50}$]

For the purposes of the present invention a "selective binding" is binding to the MCH-R1 receptor at a level at least about 10 fold greater than at the 5-$HT_{2c}$ receptor. For example, a compound with an IC-50 at MCH-R1 of 12 nM and an IC-50 at 5-$HT_{2c}$ of 1125 nM would be a compound which is a selective antagonist at the MCH-R1 receptor over the 5-$HT_{2c}$ receptor. In other treatments, methods, or compositions this value is at least about 100, while for yet other embodiments of the present invention the selectivity is at least about 1000.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, including all enantiomeric and diastereomeric forms and acceptable salts thereof, said compound having the formula:

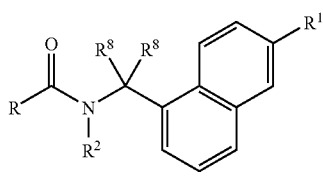

wherein R has the formula:

$R^3$ is a unit chosen from:
i) aryl units having the formula:

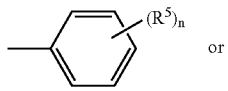

or ii) biphenyl units having the formula:

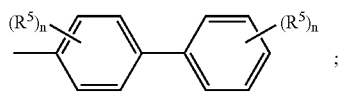

each $R^5$ is independently a substitute for hydrogen; the index x is 0 or 1; each of the indices n is from 0 to 5; $R^1$ has the formula:

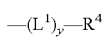

$R^4$ has the formula:

$R^6$ and $R^7$ are each independently chosen from:
i) hydrogen;
ii) $C_1$-$C_8$ substituted or unsubstituted linear, branched, or cyclic hydrocarbyl;
iii) $C_6$ or $C_{10}$ substituted or unsubstituted aryl; or
$R^6$ and $R^7$ can be taken together to form a heterocyclic ring having from 3 to 8 atoms; the index y is 0 or 1;
$R^2$ is a unit chosen from:
i) hydrogen; or
ii) $C_1$-$C_4$ linear, branched, or cyclic alkyl;
L and $L^1$ are linking units each independently having the formula:

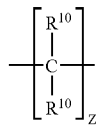

each $R^{10}$ is independently chosen from:
i) hydrogen;
ii) $C_1$-$C_6$ substituted or unsubstituted linear, branched, or cyclic hydrocarbyl;
iii) —$CO_2R^9$;
iv) —CN;
two $R^{10}$ units on the same carbon are be taken together to form a carbonyl group;
or two $R^{10}$ units from two adjacent linking units are taken together to form a double bond;
$R^9$ is hydrogen or $C_1$-$C_4$ linear, branched, or cyclic alkyl; the index z is equal to 1, 2, or 3; and
each $R^8$ is independently chosen from:
i) hydrogen;
ii) $C_1$-$C_6$ substituted or unsubstituted linear, branched, or cyclic hydrocarbyl;
iii) —$CO_2R^9$;
iv) two $R^8$ units can be taken together to form a carbonyl group.

2. A compound according to claim 1 wherein R has the formula:

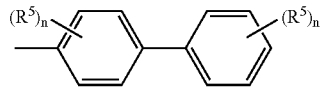

wherein each $R^5$ unit is independently one or more substitutions for hydrogen, said substitutions chosen from:
i) halogen;
ii) hydroxyl;
iii) cyano;
iv) nitro;
v) $C_1$-$C_4$ linear, branched, or cyclic alkyl;
vi) $C_1$-$C_4$ linear or branched alkoxy; and
vii) halogen substituted alkyl;
viii) —$COR^9$;
$R^4$ is hydrogen or $C_1$-$C_4$ linear, branched, or cyclic alkyl; each of the indices n is from 0 to 2.

3. A compound according to claim 2 wherein R is a unit chosen from 4-biphenyl, 4'-fluoro-4-biphenyl, 4'-chloro-4-biphenyl, 4'-cyano-4-biphenyl, 4'-hydroxy-4-biphenyl, 4'-nitro-4-biphenyl, 4'-methyl-4-biphenyl, 4'-ethyl-4-biphenyl, 4'-isopropyl-4-biphenyl, 4'-trifluoromethyl-4-biphenyl, and 4'-methoxy-4-biphenyl.

4. A compound according to claim 1 wherein L is a unit having the formula:

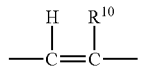

wherein each $R^{10}$ is chosen from hydrogen, methyl, ethyl, and cyano.

5. A compound according to claim 4 wherein $R^{10}$ is hydrogen.

6. A compound according to claim 5 wherein R is chosen from 4-fluorophenyl, 4-chlorophenyl, 4-hydroxyphenyl, 3-trifluoromethylphenyl, 4-trifluoromethylphenyl, 4-methoxyphenyl, and 4-nitrophenyl.

7. A compound according to claim 1 wherein $R^1$ is chosen from —$CH_2NH_2$, —$CH_2NHCH_3$, —$CH_2N(CH_3)_2$, —$CH_2NHCH_2CH_3$, —$CH_2N(CH_3)(CH_2CH_3)$, and —$CH_2N(CH_2CH_3)_2$.

8. A compound according to claim 1 wherein $R^1$ is chosen from pyrrolidin-1-ylmethyl, piperidine-1-ylmethyl, piperazine-1-ylmethyl, and morpholin-4-ylmethyl.

9. A compound according to claim 1 wherein $R^2$ is hydrogen.

10. A compound according to claim 1 wherein $R^2$ is methyl.

11. A compound according to claim 1 wherein $L^1$ is —$CH_2$—.

12. A compound according to claim 1, including all enantiomeric and diasteriomeric forms and acceptable salts thereof chosen from:
- 4'-Fluoro-biphenyl-4-carboxylic acid (6-dimethylaminomethyl-naphthalen-1-ylmethyl)-amide;
- 4'-Fluoro-biphenyl-4-carboxylic acid (6-dimethylaminomethyl-naphthalen-1-ylmethyl)-methyl-amide;
- 4'-Fluoro-biphenyl-4-carboxylic acid (6-diethylaminomethyl-naphthalen-1-ylmethyl)-methyl-amide;
- 3'-Trifluoromethyl-biphenyl-4-carboxylic acid (6-diethylaminomethyl-naphthalen-1-ylmethyl)-methyl-amide;
- Biphenyl-4-carboxylic acid (6-diethylaminomethyl-naphthalen-1-ylmethyl)-methyl-amide;
- 4-Chloro-N-(6-diethylaminomethyl-naphthalen-1-ylmethyl)-N-methyl-benzamide;
- N-(6-Diethylaminomethyl-naphthalen-1-ylmethyl)-4-fluoro-N-methyl-benzamide;
- N-(6-Diethylaminomethyl-naphthalen-1-ylmethyl)-2-methoxy-N-methyl-benzamide;
- N-(6-Diethylaminomethyl-naphthalen-1-ylmethyl)-N-methyl-4-nitro-benzamide; 9
- N-(6-Diethylaminomethyl-naphthalen-1-ylmethyl)-4-fluoro-N-methyl-3-trifluoromethyl-benzamide;
- 4'-Fluoro-biphenyl-4-carboxylic acid methyl-(6-piperidin-1-ylmethyl-naphthalen-1-ylmethyl)-amide;
- Biphenyl-4-carboxylic acid (6-piperidin-1-ylmethyl-naphthalen-1-ylmethyl)-methyl-amide;
- 2-(4'-Fluoro-biphenyl-4-yl)-N-methyl-N-(6-pyrrolidin-1-ylmethyl-naphthalen-1-ylmethyl)-acetamide;
- 4-Chloro-N-methyl-N-(6-pyrrolidin-1-ylmethyl-naphthalen-1-ylmethyl)-benzamide; and
- 2-Methoxy-N-methyl-N-(6-pyrrolidin-1-ylmethyl-naphthalen-1-ylmethyl)-benzamide.

13. A compound according to claim 1, including all enantiomeric and diasteriomeric forms and acceptable salts thereof chosen from:
- 4'-Trifluoromethyl-biphenyl-4-carboxylic acid (6-dimethylaminomethyl-naphthalen-1-ylmethyl)-methyl-amide;
- 4'-Trifluoromethyl-biphenyl-4-carboxylic acid (6-diethylaminomethyl-naphthalen-1-ylmethyl)-amide;
- 4'-Fluoro-biphenyl-4-carboxylic acid (6-diethylaminomethyl-naphthalen-1-ylmethyl)-amide;
- 3'-Trifluoromethyl-biphenyl-4-carboxylic acid (6-diethylaminomethyl-naphthalen-1-ylmethyl)-amide;
- Biphenyl-4-carboxylic acid (6-diethylaminomethyl-naphthalen-1-ylmethyl)-amide;
- 4'-Fluoro-biphenyl-4-carboxylic acid (6-piperidin-1-ylmethyl-naphthalen-1-ylmethyl)-amide;
- 4'-Trifluoromethyl-biphenyl-4-carboxylic acid (6-piperidin-1-ylmethyl-naphthalen-1-ylmethyl)-amide;
- 3'-Trifluoromethyl-biphenyl-4-carboxylic acid (6-piperidin-1-ylmethyl-naphthalen-1-ylmethyl)-amide;
- Biphenyl-4-carboxylic acid (6-piperidin-1-ylmethyl-naphthalen-1-ylmethyl)-amide;
- 4'-Trifluoromethyl-biphenyl-4-carboxylic acid (6-pyrrolidin-1-ylmethyl-naphthalen-1-ylmethyl)-amide;
- 4'-Fluoro-biphenyl-4-carboxylic acid (6-pyrrolidin-1-ylmethyl-naphthalen-1-ylmethyl)-methyl-amide;
- 3'-Trifluoromethyl-biphenyl-4-carboxylic acid (6-pyrrolidin-1-ylmethyl-naphthalen-1-ylmethyl)-amide;
- Biphenyl-4-carboxylic acid (6-pyrrolidin-1-ylmethyl-naphthalen-1-ylmethyl)-amide;
- 4'-Trifluoromethyl-biphenyl-4-carboxylic acid methyl-(6-piperidin-1-ylmethyl-naphthalen-1-ylmethyl)-methyl-amide;
- 3'-Trifluoromethyl-biphenyl-4-carboxylic acid methyl-(6-piperidin-1-ylmethyl-naphthalen-1-ylmethyl)-amide;
- 4'-Trifluoromethyl-biphenyl-4-carboxylic acid (6-diethylaminomethyl-naphthalen-1-ylmethyl)-methyl-amide; and
- 3'-Trifluoromethyl-biphenyl-4-carboxylic acid (6-diethylaminomethyl-naphthalen-1-ylmethyl)-methyl-amide.

14. A composition comprising:
A) an effective amount of one or more compounds according to claim 1; and
B) one or more excipients.

* * * * *

UNITED STATES PATENT AND TRADEMARK OFFICE
CERTIFICATE OF CORRECTION

PATENT NO.         : 7,368,462 B2                                             Page 1 of 1
APPLICATION NO. : 11/180814
DATED              : May 6, 2008
INVENTOR(S)        : Xiufeng Eric Hu It is certified that error appears in the above-identified patent and that said Letters Patent is hereby corrected as shown below:

Section 32
    Line 28, please delete "130.67" and insert -- 130.07 --.

Signed and Sealed this

Twenty-third Day of June, 2009

JOHN DOLL
*Acting Director of the United States Patent and Trademark Office*